(12) United States Patent
Khan et al.

(10) Patent No.: US 7,824,879 B2
(45) Date of Patent: Nov. 2, 2010

(54) DEVICE AND METHOD FOR MEASURING LDL-ASSOCIATED CHOLESTEROL

(75) Inventors: Shireen Khan, Castro Valley, CA (US); Suyue Qian, Fremont, CA (US); Jeff Shindelman, Castro Valley, CA (US); George E. Withers, III, Livermore, CA (US); Eileen Gee, Belmont, CA (US); William H. Chapman, Jr., Alameda, CA (US); Greg Bennett, Milpitas, CA (US); Thomas D. Schaal, San Francisco, CA (US)

(73) Assignee: Cholestech Corporation, Hayward, CA (US)

( * ) Notice: Subject to any disclaimer, the term of this patent is extended or adjusted under 35 U.S.C. 154(b) by 0 days.

(21) Appl. No.: 12/008,394

(22) Filed: Jan. 9, 2008

(65) Prior Publication Data

US 2008/0166745 A1 Jul. 10, 2008

Related U.S. Application Data

(60) Provisional application No. 60/879,631, filed on Jan. 9, 2007.

(51) Int. Cl.
*C12Q 1/60* (2006.01)
(52) U.S. Cl. .......................... 435/11; 422/58
(58) Field of Classification Search .................. 435/11, 435/962; 422/58; 436/539, 671
See application file for complete search history.

(56) References Cited

U.S. PATENT DOCUMENTS

| | | |
|---|---|---|
| 3,508,879 A | 4/1970 | Findl et al. |
| 3,607,093 A | 9/1971 | Stone |
| 3,791,933 A | 2/1974 | Moyer et al. |
| 3,797,494 A | 3/1974 | Zaffaroni |
| 3,907,642 A | 9/1975 | Richmond |
| 3,907,645 A | 9/1975 | Richmond |
| 3,925,164 A | 12/1975 | Beaucamp et al. |
| 3,983,005 A | 9/1976 | Goodhue et al. |
| 4,038,485 A | 7/1977 | Johnston et al. |
| 4,042,329 A | 8/1977 | Hochstrasser |
| 4,069,017 A | 1/1978 | Wu et al. |
| 4,125,372 A | 11/1978 | Kawai et al. |
| 4,126,416 A | 11/1978 | Sears |
| 4,144,129 A | 3/1979 | Gruber et al. |
| 4,144,306 A | 3/1979 | Figueras |
| 4,152,390 A | 5/1979 | Nosco et al. |
| 4,153,668 A | 5/1979 | Hill et al. |
| 4,164,448 A | 8/1979 | Roeschlau et al. |
| 4,181,575 A | 1/1980 | Gruber et al. |
| 4,186,251 A | 1/1980 | Tarbutton |
| 4,188,188 A | 2/1980 | Willner et al. |
| 4,212,938 A | 7/1980 | Gruber et al. |
| 4,215,993 A | 8/1980 | Sanders |
| 4,216,245 A | 8/1980 | Johnson |
| 4,234,317 A | 11/1980 | Lucas et al. |
| 4,246,339 A | 1/1981 | Cole et al. |
| 4,248,829 A | 2/1981 | Kitajima et al. |
| 4,256,693 A | 3/1981 | Kondo et al. |
| 4,271,119 A | 6/1981 | Columbus |
| 4,313,734 A | 2/1982 | Leuvering |
| 4,366,244 A | 12/1982 | Pascal |
| 4,391,904 A | 7/1983 | Litman et al. |
| 4,399,362 A | 8/1983 | Cormier et al. |
| 4,435,504 A | 3/1984 | Zuk et al. |
| 4,477,575 A | 10/1984 | Vogel et al. |
| 4,503,144 A | 3/1985 | Deeg et al. |
| 4,533,629 A | 8/1985 | Litman et al. |
| 4,544,630 A | 10/1985 | Ziegenhorn et al. |
| 4,549,655 A | 10/1985 | Forsythe et al. |
| 4,552,839 A | 11/1985 | Gould et al. |
| 4,565,740 A | 1/1986 | Golander et al. |
| 4,615,946 A | 10/1986 | Temple |
| 4,623,628 A | 11/1986 | Maaskant et al. |
| 4,632,901 A | 12/1986 | Valkirs et al. |
| 4,654,310 A | 3/1987 | Ly |
| 4,680,259 A | 7/1987 | Cumbo et al. |
| 4,743,560 A | 5/1988 | Campbell |
| 4,746,605 A | 5/1988 | Kerscher et al. |
| 4,756,828 A | 7/1988 | Litman et al. |
| 4,774,192 A | 9/1988 | Terminiello et al. |
| 4,814,077 A | 3/1989 | Furuyoshi et al. |
| 4,816,224 A | 3/1989 | Vogel et al. |
| 4,820,489 A | 4/1989 | Rothe et al. |

(Continued)

FOREIGN PATENT DOCUMENTS

CA 1211707 A 9/1986

(Continued)

OTHER PUBLICATIONS

Bachorik, et al. Precipitation Methods for Quantification of Lipoproteins. Methods in Enzymology. Academic Press, Inc. 1986;129:78-100.

(Continued)

*Primary Examiner*—Ralph Gitomer
(74) *Attorney, Agent, or Firm*—Wilson Sonsini Goodrich & Rosati

(57) ABSTRACT

An assay device and method for determining the concentration of low density lipoprotein (LDL)-associated cholesterol (LDL-C) in a body-fluid sample, such as a blood sample is described.

25 Claims, 8 Drawing Sheets

U.S. PATENT DOCUMENTS

| | | | |
|---|---|---|---|
| 4,826,421 A | 5/1989 | Asano et al. |
| 4,826,721 A | 5/1989 | Obrecht et al. |
| 4,826,759 A | 5/1989 | Guire et al. |
| 4,826,761 A | 5/1989 | Arai et al. |
| 4,828,983 A | 5/1989 | Mcclune |
| 4,839,296 A | 6/1989 | Kennedy et al. |
| 4,839,297 A | 6/1989 | Freitag et al. |
| 4,849,340 A | 7/1989 | Oberhardt |
| 4,855,108 A | 8/1989 | Masuda et al. |
| 4,877,586 A | 10/1989 | Devaney, Jr. et al. |
| 4,877,746 A | 10/1989 | Jansson et al. |
| 4,910,134 A | 3/1990 | Yamanishi et al. |
| 4,920,046 A | 4/1990 | Mcfarland et al. |
| 4,943,522 A | 7/1990 | Eisinger et al. |
| 4,956,275 A | 9/1990 | Zuk et al. |
| 4,959,324 A | 9/1990 | Ramel et al. |
| 4,963,468 A | 10/1990 | Olson |
| 4,973,549 A | 11/1990 | Khanna et al. |
| 4,981,786 A | 1/1991 | Dafforn et al. |
| 4,987,085 A | 1/1991 | Allen et al. |
| 4,999,285 A | 3/1991 | Stiso |
| 4,999,287 A | 3/1991 | Allen et al. |
| 4,999,289 A | 3/1991 | Akiba |
| 5,075,078 A | 12/1991 | Osikowicz |
| 5,082,626 A | 1/1992 | Grage, Jr. |
| 5,087,556 A | 2/1992 | Ertinghausen |
| 5,110,724 A | 5/1992 | Hewett |
| 5,130,231 A | 7/1992 | Kennedy et al. |
| 5,135,716 A | 8/1992 | Thakore |
| 5,135,873 A | 8/1992 | Patel et al. |
| 5,137,808 A | 8/1992 | Ullman et al. |
| 5,144,350 A | 9/1992 | Takahashi et al. |
| 5,147,609 A | 9/1992 | Grenner |
| 5,149,505 A | 9/1992 | Englishe et al. |
| 5,156,954 A | 10/1992 | Mielke |
| 5,167,922 A | 12/1992 | Long |
| 5,171,688 A | 12/1992 | Hewett et al. |
| 5,204,063 A | 4/1993 | Allen |
| 5,213,964 A | 5/1993 | Jones |
| 5,213,965 A | 5/1993 | Jones |
| 5,215,886 A | 6/1993 | Patel et al. |
| 5,252,496 A | 10/1993 | Kang et al. |
| 5,260,221 A | 11/1993 | Ramel et al. |
| 5,260,222 A | 11/1993 | Patel et al. |
| 5,286,626 A | 2/1994 | Law et al. |
| 5,316,916 A | 5/1994 | Jones et al. |
| 5,320,968 A | 6/1994 | Seman et al. |
| 5,401,466 A * | 3/1995 | Foltz et al. ............ 422/56 |
| 5,407,836 A | 4/1995 | Ziegenhorn et al. |
| 5,409,664 A | 4/1995 | Allen |
| 5,411,870 A | 5/1995 | Law et al. |
| 5,416,000 A | 5/1995 | Allen et al. |
| 5,417,863 A | 5/1995 | Varaday et al. |
| 5,426,030 A | 6/1995 | Rittersdorf et al. |
| 5,451,370 A | 9/1995 | Jones |
| 5,460,974 A | 10/1995 | Kozak et al. |
| 5,468,647 A | 11/1995 | Skold et al. |
| 5,482,839 A | 1/1996 | Ashihara et al. |
| 5,496,637 A | 3/1996 | Parham et al. |
| 5,543,054 A | 8/1996 | Charkoudian et al. |
| 5,559,041 A | 9/1996 | Kang et al. |
| 5,580,743 A | 12/1996 | Rittersdorf et al. |
| 5,591,645 A | 1/1997 | Rosenstein |
| 5,591,646 A | 1/1997 | Hudson et al. |
| 5,611,995 A | 3/1997 | De Zoeten et al. |
| 5,622,871 A | 4/1997 | May et al. |
| 5,633,168 A | 5/1997 | Glasscock et al. |
| 5,654,162 A | 8/1997 | Guire et al. |
| 5,656,503 A | 8/1997 | May et al. |
| 5,695,947 A | 12/1997 | Guo et al. |
| 5,714,389 A | 2/1998 | Charlton et al. |
| 5,726,010 A | 3/1998 | Clark |
| 5,726,013 A | 3/1998 | Clark |
| 5,728,352 A | 3/1998 | Poto et al. |
| 5,744,096 A | 4/1998 | Jones et al. |
| 5,786,164 A | 7/1998 | Rittersdorf et al. |
| 5,788,942 A | 8/1998 | Kitani et al. |
| 5,989,921 A | 11/1999 | Charlton et al. |
| 6,027,943 A | 2/2000 | Kang et al. |
| 6,107,045 A | 8/2000 | Koren et al. |
| 6,156,492 A | 12/2000 | Kobayashi et al. |
| 6,159,424 A | 12/2000 | Kauhaniemi et al. |
| 6,171,849 B1 | 1/2001 | Rittersdorf et al. |
| 6,187,598 B1 | 2/2001 | May et al. |
| 6,194,225 B1 | 2/2001 | Oka et al. |
| 6,210,907 B1 | 4/2001 | Cha |
| 6,214,570 B1 | 4/2001 | Rittersdorf et al. |
| 6,228,660 B1 | 5/2001 | May et al. |
| RE37,437 E | 11/2001 | Friesen et al. |
| 6,352,862 B1 | 3/2002 | Davis et al. |
| RE37,701 E | 5/2002 | Bahar et al. |
| 6,406,920 B1 | 6/2002 | Davis et al. |
| 6,596,112 B1 | 7/2003 | Ditter et al. |
| 6,844,149 B2 | 1/2005 | Goldman |
| 6,881,581 B2 | 4/2005 | Jones et al. |
| 7,087,397 B2 | 8/2006 | Anaokar et al. |
| 7,195,921 B2 | 3/2007 | Jones et al. |
| 7,220,595 B2 | 5/2007 | Nugent |
| 7,223,546 B2 * | 5/2007 | Miki et al. ............ 435/7.1 |
| 7,238,519 B2 | 7/2007 | Bellet |
| 7,476,548 B2 * | 1/2009 | Blatt et al. ............ 436/514 |
| 7,491,542 B2 * | 2/2009 | Scheuringer ............ 436/71 |
| 2003/0012905 A1 | 1/2003 | Zumbrum et al. |
| 2003/0166291 A1 | 9/2003 | Jones et al. |
| 2003/0175153 A1 | 9/2003 | Anaokar et al. |
| 2003/0224471 A1 | 12/2003 | Jones et al. |
| 2004/0023400 A1 | 2/2004 | Tamura et al. |
| 2004/0029293 A1 | 2/2004 | Nugent |
| 2004/0126830 A1 * | 7/2004 | Shull et al. ............ 435/11 |
| 2004/0235182 A1 | 11/2004 | Jones et al. |
| 2005/0124019 A1 | 6/2005 | Jones |
| 2005/0147532 A1 | 7/2005 | Bellet |
| 2005/0208609 A1 | 9/2005 | Jones et al. |
| 2005/0214161 A1 * | 9/2005 | Gupta ............ 422/56 |
| 2005/0221502 A1 * | 10/2005 | Shindelman et al. ...... 436/514 |
| 2006/0051738 A1 * | 3/2006 | Zweig ............ 435/4 |

FOREIGN PATENT DOCUMENTS

| | | |
|---|---|---|
| DE | 2727347 A1 | 12/1977 |
| DE | 3130749 A1 | 2/1983 |
| DE | 10204606 C1 | 10/2003 |
| EP | 0045476 A1 | 2/1982 |
| EP | 0146654 A2 | 7/1985 |
| EP | 0146654 A3 | 7/1985 |
| EP | 0176357 A1 | 4/1986 |
| EP | 0229982 A2 | 7/1989 |
| EP | 0229982 A3 | 7/1989 |
| EP | 0353570 A2 | 2/1990 |
| EP | 0353570 A3 | 2/1990 |
| EP | 0357400 A2 | 3/1990 |
| EP | 0408223 A1 | 1/1991 |
| EP | 0357400 A3 | 4/1991 |
| EP | 0627627 A1 | 12/1994 |
| EP | 0408223 B1 | 3/1995 |
| EP | 0415298 B1 | 11/1995 |
| EP | 0740157 A2 | 10/1996 |
| EP | 0740157 A3 | 5/1998 |
| EP | 1028319 A2 | 8/2000 |
| EP | 1029928 A2 | 8/2000 |
| EP | 1029928 A3 | 9/2002 |
| EP | 1357383 A1 | 10/2003 |
| EP | 1028319 A3 | 1/2004 |
| GB | 2090659 A | 7/1982 |

| | | | |
|---|---|---|---|
| JP | 2-210265 A | 8/1990 | |
| JP | 3-99268 A | 4/1991 | |
| WO | WO 83/00931 A1 | 3/1983 | |
| WO | WO 90/10869 A1 | 9/1990 | |
| WO | WO 93/13856 A1 | 7/1993 | |
| WO | WO 94/12879 A1 | 6/1994 | |
| WO | WO 96/04556 A1 | 2/1996 | |
| WO | WO 96/15453 A1 | 5/1996 | |
| WO | WO 89/05458 A1 | 6/1998 | |
| WO | WO 98/37416 A1 | 8/1998 | |
| WO | WO 99/58966 A1 | 11/1999 | |
| WO | WO 00/42434 A1 | 7/2000 | |
| WO | WO 02/02796 A2 | 1/2002 | |
| WO | WO 02/02796 A3 | 1/2002 | |
| WO | WO 02/20142 A1 | 3/2002 | |
| WO | WO 2004/025265 A2 | 3/2004 | |
| WO | WO 2004/025265 A3 | 7/2004 | |

OTHER PUBLICATIONS

Chandler, et al. The place of gold in rapid tests. IVD Technology. 2000; 6(2):37-49.

De Maat et al. Effect of fish oil and vitamin E on the cardiovascular risk indicators fibrinogen, C-reactive protein and PAI activity in healthy young volunteers. Fibrinolysis. 1994; 8(Suppl 2):50-52.

European search report Nov. 12, 2003 for Application No. 2022910.0.

European search report Sep. 5, 2005 for Application No. 03757364.9.

European search report dated Jan. 26, 2004 for Application No. 3025724.0.

European search report dated Nov. 17, 1994 for Application No. 92913182.9.

European search report dated Feb. 6, 1991 for Application No. 89308774.2.

European search report dated May 26, 2003 for Application No. 2013433.4.

European search report dated Jul. 24, 2003 for Application No. 2004339.4.

Fless, et al. Enzyme-linked immunoassay for Lp[a]. J Lipid Res. May 1989;30(5):651-62.

Grau, et al. Clinical and biochemical analysis in infection-associated stroke. Stroke. Sep. 1995;26(9):1520-6.

Hegele, R. Lipoprotein (a): an emerging risk factor for atherosclerosis. Can. J. Cardiol. 1989;5:263-265.

International search report dated Feb. 11, 2004 for PCT Application No. US2003/17792.

International search report May 24, 2005 for PCT Application No. IB2004/003704.

International search report Jul. 11, 1990 for PCT Application No. US1990/01249.

International search report dated Jan. 31, 1992 for PCT Application No. US1991/05004.

International Search Report dated Oct. 24, 2005 for PCT Application No. US05/11093.

International search report dated Dec. 8, 1989 for PCT Application No. US1989/03730.

International search report dated Apr. 2, 2008 for PCT Application No. US2008/000344.

International search report dated Jun. 23, 1998 for PCT Application No. US1998/02952.

International search report dated Jul. 14, 2006 for PCT Application No. US2005/045038.

International Search Report dated Aug. 15, 2003 for PCT Application No. PCT/US03/01354.

International search report dated Aug. 28, 1992 for PCT Application No. US1992/04302.

International search report dated Sep. 17, 2003 for PCT Application No. US2003/10420.

International Search report from PCT/US2004/010001 dated Aug. 16, 2004.

Kuller, et al. Relation of C-reactive protein and coronary heart disease in the MRFIT nested case-control study. Multiple Risk Factor Intervention Trial. Am J Epidemiol. Sep. 15, 1996;144(6):537-47.

Litman, et al. An internally referenced test strip immunoassay for morphine. Clin. Chem. 1983;29(9):1598-1603.

Liuzzo, et al. The prognostic value of C-reactive protein and serum amyloid a protein in severe unstable angina. N Engl J Med. Aug. 18, 1994;331(7):417-24.

McNamara, et al. Immunoseparation method for measuring low-density lipoprotein cholesterol directly from serum evaluated. Clinical chemistry. 1995;41(2):232-240.

Mendall, et al. C reactive protein and its relation to cardiovascular risk factors: a population based cross sectional study. BMJ. Apr. 27, 1996;312(7038):1061-1065.

Nauck, et al. Analytical and clinical performance of a detergent-based homogeneous LDL-cholesterol assay: a multicenter evaluation. Clin Chem. Apr. 2000;46(4):506-14.

Paek, et al. Immunochromatographic membrane strip assay system for a single-class plasma lipoprotein cholesterol, exemplified by high-density lipoprotein cholesterol measurement. Biotechnol Bioeng. Jan. 20, 1999;62(2):145-54.

Seman, et al. Quantification of lipoprotein(a) in plasma by assaying cholesterol in lectin-bound plasma fraction. Clin Chem. Mar. 1994;40(3):400-3.

Sugiuchi, et al. Homogeneous assay for measuring low-density lipoprotein cholesterol in serum with triblock copolymer and alpha-cyclodextrin sulfate. Clin Chem. Mar. 1998;44(3):522-31.

Thompson, et al. Hemostatic factors and the risk of myocardial infarction or sudden death in patients with angina pectoris. European Concerted Action on Thrombosis and Disabilities Angina Pectoris Study Group. N Engl J Med. Mar. 9, 1995;332(10):635-41.

Tracy, et al. C-reactive protein and incidence of cardiovascular disease in older women: the rural health promotion project and the cardiovascular health study. Circulation. Feb. 1, 1996; 93(3):622, abstract 8. (Abstracts of the 36th annual conference on cardiovascular disease epidemiology and prevention, Mar. 13-15, 1996. Fairmont Hotel, San Francisco, CA.).

* cited by examiner

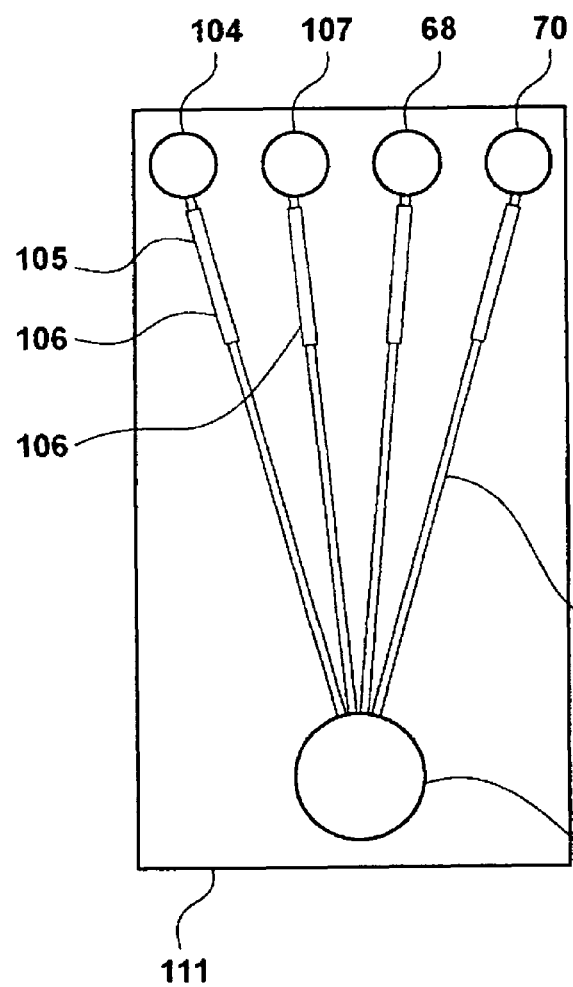
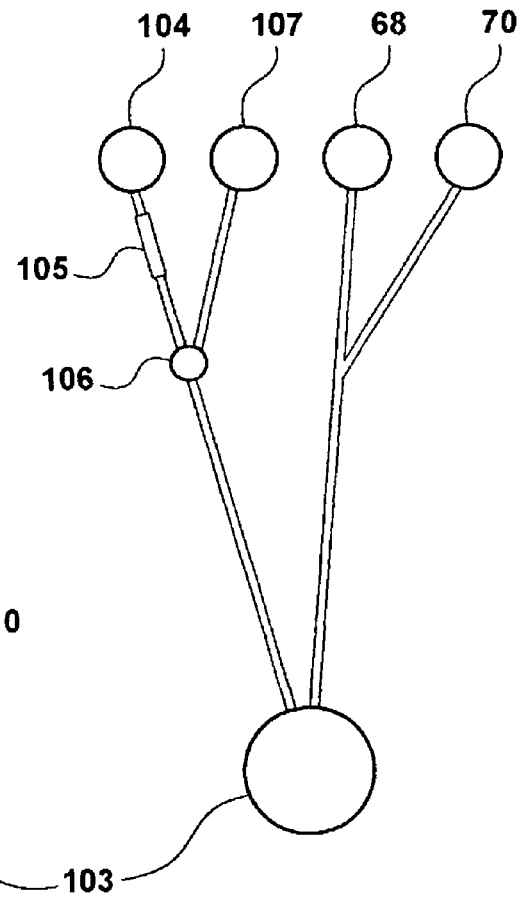
FIG. 1G          FIG. 1H

DEVICE AND METHOD FOR MEASURING LDL-ASSOCIATED CHOLESTEROL

This application claims the benefit of U.S. Provisional Application No. 60/879,631, filed Jan. 9, 2007, which is incorporated herewith by reference in its entirety.

TECHNICAL FIELD

The present disclosure relates to assay devices and methods for determining the concentration of low density lipoprotein (LDL)-associated cholesterol (LDL-C) in a body-fluid sample, such as a blood sample.

REFERENCES

Cole, T. G. (1996) *Journal of Clinical Ligand Assay* 19:168-171.
Gromoll, B. et al. (1989) *Zeitschrift fur Medizinische Laboratoriumsdiagnostik* 30:445-9.
Kerscher, L. et al. (1988) U.S. Pat. No. 4,746,605.
Nauck, M. et al. (2000) *Clin. Chem.* 46:506-514.
Kerscher, L. et al. (1985) *Clin Biochem* 18:118-25.
Sugiuchi, H. et al. (1998) *Clin. Chem.* 44:522-531.
Ziegenhorn, J. et al. (1995) U.S. Pat. No. 5,407,836.

BACKGROUND

Cholesterol circulates in the blood predominantly in protein-bound form. The proteins which transport cholesterol are lipoproteins, which are subdivided into classes based on their density. High-density lipoproteins (HDL), which typically account for about 20-30% of serum cholesterol, are involved in the catabolism of triglyceride-rich lipoproteins and in the removal of cholesterol from peripheral tissues and transport to the liver. The very-low density lipoproteins (VLDL) are triglyceride-rich lipoproteins which are synthesized in the liver and ultimately converted to low-density lipoproteins (LDL), which transport most of the plasma cholesterol in humans. Chylomicrons are a type of very low density lipoproteins that are synthesized in the intestinal mucosa and transport exogenous (dietary) cholesterol and triglycerides from the small intestine to muscle and adipose tissues. VLDL typically accounts for about 5% of total serum cholesterol, while LDL typically accounts for about 60-75%. However, diets high in saturated fat and cholesterol can cause an increase in the amount of LDL cholesterol in the blood.

A relationship between serum levels of different lipoproteins and risk of coronary disease has been established. In particular, if the proportion of serum cholesterol associated with LDL is high and/or the proportion associate with HDL is low, the risk of coronary disease is increased. In view of the importance of relative serum cholesterol levels in risk assessment and management of atherogenic disease, considerable effort has been spent screening large populations of both normal and high-risk individuals for serum levels of HDL, LDL, as well as total cholesterol and triglycerides. The effectiveness of treatments of high-risk individuals has been monitored by regular testing of serum levels of cholesterol in the various lipoprotein compartments.

LDL-associated cholesterol is often measured indirectly by separately determining total serum cholesterol, triglycerides, and HDL associated cholesterol. Various methods have been proposed for direct quantification of LDL. The different lipoproteins can be separated by ultracentrifugation, which is a generally accurate method for determining LDL, but impractical for clinical use. A series of patents by Ziegenhorn et al. (U.S. Pat. No. 4,746,605 (1988), U.S. Pat. No. 5,407,836 (1995), and U.S. Pat. No. 5,532,172 (1996)) describe a method in which HDL is removed from a serum sample by addition of an anti-HDL antibody, and triglyceride-rich very low density lipoproteins (VLDL) are removed by precipitation with an anionic polymer, e.g., dextran sulfate, leaving LDL in solution for independent quantification. However, this method requires manipulation of several solutions and typically employs centrifugation to remove the antibody-bound or precipitated lipoproteins.

Reports by Sugiuchi et al. (1998) and Nauck et al. (2000) describe a homogenous solution assay in which an anionic polymer, e.g., cyclodextrin sulfate, is used to reduce reactivity of VLDL and chylomicron cholesterol without precipitation, while a nonionic surfactant such as PEO/PPO is used to solubilize, and thus increase the reactivity of, cholesterol in LDL particles. The Direct LDL assay developed by Genzyme (see, e.g., NcNamara et al., 1995; Cole, 1996) employs antibodies directed to VLDL and HDL to bind these lipoproteins, followed by centrifuging and filtering to recover the supernatant containing LDL.

A widely accepted assay for the epidemiological study of cholesterol fractions and cardiac risk assessment is the beta-quantification method which uses fractionation of lipoproteins by ultracentrifugation. Serum samples are centrifuged for approximately 18 hours in a preparative ultracentrifuge to fractionate the chylomicrons and VLDLs from the LDLs and HDLs. The Total Cholesterol minus chylomicrons and VLDLs (TCm) is determined from the HDL/LDL fraction. The HDL is determined following selective precipitation and removal of LDL. The LDL is calculated using the equation LDL=TCm−HDL. The beta-quantification method is independent of triglycerides (TG) and can be used for fasting and non-fasting patients. However, this method is time consuming, laborious, and not conducive to routine use due to the limited number of samples that can be centrifuged at a time.

These liquid-phase assays have a number of limitations with respect to their use in widespread screening. First, the methods generally require a venous blood sample, requiring a trained technician to draw, fractionate and aliquot the blood sample. The sample must be treated with reagents such as precipitating agent, binding agent, surfactant, and, in most cases, further processed to remove precipitated material. Although some of these procedures can be automated, analytical machines designed for this purpose are expensive and not widely available outside of large hospitals.

It is therefore desirable to provide an automated, self-contained assay device for rapidly and accurately determining the levels of LDL in a blood or serum sample.

SUMMARY

In one aspect, an assay device for determining the amount of LDL-associated cholesterol in a blood-fluid sample containing very low density lipoprotein (VLDL), chylomicrons, low-density lipoprotein (LDL), high-density lipoproteins (HDL), and triglycerides is described. The assay device comprises (a) a body having a sample well for receiving such a sample; (b) first and second detection zones mounted on said body for producing a detectable product related to the amount of HDL and an adjusted total cholesterol composed of HDL plus LDL, respectively, in said sample fluid, (c) fluid flow pathways for transferring sample fluid from the sample well to said detection zones, and (d) reagents in one or more of said flowpaths, and optionally, in said sample well, for selectively removing VLDL and chylomicrons in sample fluid transferred from the sample well to the first and second detection zones, and for selectively removing LDL in sample fluid transferred from the sample well to the second detection zone. In an embodiment, the assay device further comprises a third detection zone mounted on said body for producing a detectable product related to the amount of TG in said sample fluid; and a fourth detection zone mounted on said body for producing a detectable product related to the amount of total cholesterol in said sample fluid.

In an embodiment where the device is in a dry-strip cassette format, (i) the fluid pathways include at least one dry-strip spreading layer for transferring sample fluid from the sample well to the first and second detection zones, and (ii) the first and second detection zones include first and second reaction pads, respectively. The first and second reaction pads are carried on a reaction bar that is mounted on said body for movement toward and away from the body, to bring the pads into contact with the at least one spreading layer, to transfer sample fluid from the spreading layers to the pads. In another embodiment, the third and fourth detection zones include third and fourth reaction pads, respectively, carried on a reaction bar that is mounted on the body for movement toward and away from the body, to bring the pads into contact with at least one spreading layer, to transfer sample fluid from the spreading layer to the pads.

In an embodiment, the first and second reaction pads contain reagents for producing a detectable product related to the amount of free and lipoprotein-associated cholesterol in the pads. In another embodiment, the third reaction pad contains reagents for producing a detectable product related to the amount of triglycerides in the pad, and the fourth reaction pad includes reagents for producing a detectable product related to the amount of free and lipoprotein-associated cholesterol in the pad.

In a further embodiment, the reagents for selectively removing VLDL and chylomicrons in sample fluid transferred from the sample well to the first and second reaction pads are contained in a dry-strip flap that provides fluid communication between the sample well and the at least one spreading layer, and the reagents for selectively removing LDL in sample fluid transferred from the sample well to the first reaction pad are contained in a filter pad carried on the reaction bar, immediately upstream of the first reaction pad. Alternatively, the reagents for selectively removing VLDL and chylomicrons in sample fluid transferred from the sample well to the second reaction pads are contained in a filter pad carried on said reaction bar, immediately upstream of the second reaction pad, and the reagents for selectively removing LDL in sample fluid transferred from the sample well to the first reaction pad are contained in a filter pad carried on the reaction bar, immediately upstream of the first reaction pad.

In an embodiment, where the reaction bar is movable toward the body from a first position to a second position, to bring the flap into a position of fluid communication between the sample well and the at least one spreading layer, and from the second position to a third position, to bring the reaction pads into contact with the at least one spreading layer. In another embodiment, the reaction bar is movable toward the body from a first position to a second position, to bring the reaction pads into contact with the at least one spreading layer.

Where the device is in a microfluidics format, the fluid pathways include a plurality of microchannels for transferring sample fluid from the sample well to the first and second detection zones, and the first and second reaction zones are formed in the body. In another embodiment, the fluid pathways include a plurality of microchannels for transferring sample fluid from the sample well to the third and fourth detection zones, and the third and fourth reaction zone is formed in the body. The first and second detection zones may contain reagents for producing a detectable product related to the amount of free and lipoprotein-associated cholesterol. The third detection zone may contain reagents for producing a detectable product related to the amount of triglycerides, and the fourth detection zone contains reagents for producing a detectable product related to the amount of free and lipoprotein-associated cholesterol. In another embodiment, the reagents for selectively removing VLDL and chylomicrons in sample fluid transferred from the sample well to the first and second detection zones include affinity binding reagents in the first microchannel upstream of the first and second detection zones, and the reagents for selectively removing LDL in sample fluid transferred from the sample well to the second detection zone include affinity binding reagent contained in a region of the first microchannel between the first and second detection zones and downstream of the second detection zone.

In another aspect, an apparatus for determining the amount of LDL-associated cholesterol in a body-fluid sample containing very low density lipoprotein (VLDL), chylomicrons, low-density lipoprotein (LDL) and high-density lipoproteins (HDL) is described. The apparatus comprises (a) the device of claim 1, and (b) a device reader having (i) a device holder for receiving the cassette, (ii) a sensor for measuring the amount of detectable product produced in the first and second zones of the device, and (iii) a processor operably connected to the sensor for determining sample amounts of HDL and adjusted total cholesterol and for calculating sample LDL level based on determined levels of HDL and adjusted total cholesterol. In an embodiment, the sensor is configured to measure the amount of detectable product produced in a third and fourth zone of the device, and the processor is operably connected to the sensor for determining sample amounts of triglycerides and total cholesterol, respectively. In another embodiment, the processor is operable to determine sample LDL level based on the difference between total adjusted cholesterol and HDL, when the detected level of triglycerides is above an established triglycerides level, and based on the difference between total cholesterol and HDL plus an adjusted triglyceride value, according to the Friedewald equation, when the detected level of triglycerides is below such established level. In an embodiment, the processor is operable to determine sample LDL level from a lookup table whose LDL values are based on the difference between total adjusted cholesterol and HDL, when the detected level of triglycerides is above an established triglycerides level, and based on the difference between total cholesterol and HDL plus an adjusted triglyceride value, according to the Friedewald equation, when the detected level of triglycerides is below such established level. In another embodiment, the processor is operable to determine sample LDL level from an algorithm which calculates LDL values based on the difference between total adjusted cholesterol and HDL, when the detected level of triglycerides is above an established triglycerides level, and based on the difference between total cholesterol and HDL plus an adjusted triglyceride value, according to the Friedewald equation, when the detected level of triglycerides is below such established level.

In a further aspect, a method for determining the amount of LDL-associated cholesterol in a blood-fluid sample containing very low density lipoprotein (VLDL), chylomicrons, low-density lipoprotein (LDL), high-density lipoproteins (HDL), and triglycerides is described. The method comprises (a) measuring the levels of HDL and an adjusted total cholesterol composed of HDL plus LDL, respectively, in such a sample fluid, and (b) determining sample LDL level based on the difference between total adjusted cholesterol and HDL. In an embodiment, the method further includes measuring the levels of total cholesterol, and triglycerides, and when the detected level of triglycerides is above an established triglyceride level, the determining sample LDL level is based on the difference between total adjusted cholesterol and HDL, and the determining is based on the difference between total cholesterol and HDL plus an adjusted triglyceride value, according to the Friedewald equation, when the detected level of triglycerides is below such established level.

These and other objects and features of the invention will become more fully apparent when the following detailed description of the invention is read in conjunction with the accompanying drawings. It will be appreciated that aspects and embodiments may be interchanged.

BRIEF DESCRIPTION OF THE DRAWINGS

FIGS. 1G and 1H are top views of microfluidics embodiments of the device of the present disclosure.

DETAILED DESCRIPTION

Figure 1A:
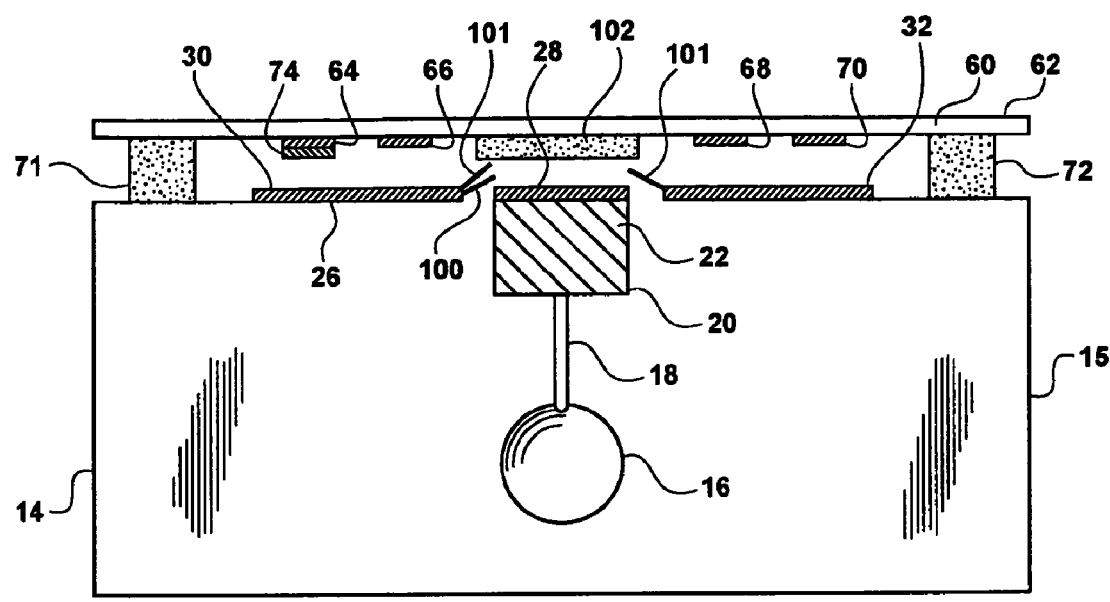
FIGS. 1A-1F are side views of cassette embodiments of the device. The features of the various cassette embodiments are described in the text.

All publications, patents, patent applications or other references cited in this application are herein incorporated by reference in their entirety as if each individual publication, patent, patent application or reference are specifically and individually indicated to be incorporated by reference.

I. Definitions

The following terms have the following meanings unless indicated otherwise.

A first element is in "fluid communication" or "fluid contact" with a second element when a fluid is able to travel from the first to the second element, via a path of contiguous solid elements, under the impetus of capillary action and/or gravity. The first and second elements may be in direct contact, or elements through which the fluid can pass may be intervening, as long as the first and second elements are connected by a contiguous path of solid elements. As described herein, these intervening elements may contain reagents.

An element is "not in fluid communication (or contact)" with another element when a fluid is not able to travel from one element to the other via capillary action and/or gravity. Typically, the elements are physically separated, i.e. spaced apart and/or separated by a region that does not transport fluid.

Two elements in an assay device that are "adjacent" are positioned such that, during the assay procedure, sample flows from one to the other without contacting any intervening reagent-containing element.

"Reagent-containing" refers to reagent(s) initially present in an element, e.g., by impregnation or immobilization, and not to reagent that might be introduced by sample flowing into the element.

A "reagent pad," or assay pad, as used herein, may comprise any material, such as a porous membrane or fibrous strip, which can contain impregnated or immobilized reagents and through which fluid can move via capillary action and/or gravity. Exemplary materials for reagent pads include porous, fused polymer or microporous polymer membranes, such as polysulfone, polypropylene, nylon, nitrocellulose, Teflon®, or polyvinylchloride microporous membranes. In some embodiments, the reagent pad material is polysulfone. Absorbent material, such as nitrocellulose, may be cast onto a sheet of clear Mylar® or similar material. The reagent pad may be supported on a foam support. Exemplary reaction pads have a thickness of about 100-150 μm and side dimensions of about 3 mm. In some embodiments, the absorption volume of each pad is between about 0.5-1.0 μl. The reaction pads may be asymmetric membranes; that is, membranes having a porosity gradient across the thickness of the membrane. In this case, the smaller pored side of the membrane may face upward, such that this side is observed for detection. Reaction pads may be inserted into windows of a support bar, affixed to a transparent support bar (e.g., via a transparent or translucent adhesive material, or by sonic welding or other suitable bonding method), or otherwise attached to support structure and adapted for reading by an instrument or human. At least some reagent pads may contain reagents for assaying lipid levels in a biological sample.

"Reagent pads" are generally provided in "detection zones," which are locations within the body of a device where a particular lipoprotein fraction can be found and is therefore available to interact with a detection reagent, e.g., provided on a reagent pad. Thus a particular reagent pad (which may be affixed to reaction bar) occupies, or in operation is moved to occupy, a particular detection zone, although the terms may also be used interchangeably. Generally, the first detection zone corresponds to the HDL reaction pad, the second detection zone correspond to the TCm reaction pad (a measure of HDL+LDL), the third detection zone corresponds to the TC reaction pad (optional), and the fourth detection corresponds to the TG reaction pad (optional). TCm is also referred to herein as an adjusted total cholesterol. It will be appreciated that the HDL reaction pad, TCm reaction pad, TC reaction pad (where included), and TG reaction pad (where included).

As used herein, "HDL-C" means HDL-associated cholesterol and "LDL-C" means LDL-associated cholesterol. It is understood that HDL and LDL contain cholesterol, regardless of the "-C" suffix.

As used herein, "measuring" or "detecting" cholesterol means determining the quantity of cholesterol in a sample using chemical assays described herein and known in the art. The cholesterol may be in HDL, LDL, VLDL, or chylomicrons. Such reagents include, but are not limited to, cholesterol esterase, for releasing free cholesterol from the lipoprotein, cholesterol oxidase, for producing $H_2O_2$ by reaction with free cholesterol, peroxidase, and a coupled dye system which is converted, in the presence of peroxidase and $H_2O_2$, to a distinctively colored signal reaction product. Evolved $H_2O_2$ can also be measured by a biosensor, as described, for example, in co-owned US App. Pub. No. 2003/0224471 and in PCT Pub. No. WO 99/58966 (Dobson et al.), which are incorporated herein by reference. If desired, selected assay reagents, e.g., peroxidase, may be immobilized to the test pad membrane, according to well known methods for enzyme immobilization (see, e.g., U.S. Pat. No. 4,999,287; U.S. Pat. No. 5,419,902; Blum, L. J. et al., *Anal. Lett.* 20:317-326 (1987); Kiang, S. W. et al., *Clin. Chem.* 22:1378-82 (1976); Guilbault, G. G., Ed., *Modern Monographs in Analytical Chemistry, Vol. 2: Analytical Uses of Immobilized Enzymes* (1984); Torchilin, V. P., *Progress in Clinical Biochemistry and Medicine, Vol.* 11: *Immobilized Enzymes in Medicine.*

As used herein, "measuring" or "detecting" triglycerides (TG) means determining the quantity of TG in a sample using reagents. Exemplary reagents include, but are not limited to, lipase, L-glycerol kinase, and L-glycerol-3-phosphate oxidase, for generating $H_2O_2$ from triglyceride, via the intermediate L-glycerol-3-phosphate.

As used herein, "precipitation reagents" include sulfonated polysaccharides, heparin, and phosphotungstate, in the presence or absence of a group II cation, such as $Mg^{2+}$, $Mn^{2+}$, or $Ca^{2+}$. Selective VLDL precipitation has been described using, for example, phosphotungstic acid/$MgCl_2$ (see, e.g., H. Schriewer et al., *J. Clin. Chem. & Clin. Biochem.* 22:35-40, 1984), heparin/$MnCl_2$ (see, e.g., S. M. Lamplugh et al., *Clinica chimica acta* 86:31-6, 1978), heparin/$MgCl_2$ (see, e.g., Uterman et al., Gromoll et al., both cited above), and dextran sulfate/$CaCl_2$ (see, e.g., Kerscher et al., cited above). In general, a lower concentration of reagent is used than would be used to precipitate VLDL and LDL together. The effectiveness of a particular reagent system and concentration can be determined using methods known in the art. For example, a precipitation reagent containing 130 mM $Mg(OAc)_2$ and 0.15% heparin was found to precipitate the majority of VLDL and chylomicrons from a serum sample without precipitating significant amounts of LDL. A reagent containing about 28 mg/mL dextran sulfate, MW 5,000-50,000 (sodium salt) and about 62 mM $MgSO_4$ is effective in precipitating VLDL and chylomicrons. Precipitation of VLDL and chylomicrons are assessed by measuring triglycerides in the sample before and after exposure to the reagent. To determine precipitation efficiency, triglyceride (TG) levels are measured to confirm that VLDL and chylomicrons were removed. Then, LDL levels obtained by measuring HDL and TCm in the sample and then subtracting HDL from TCm are compared with starting LDL levels that are determined separately. An exemplary method uses a Beckman Synchron analyzer to determine the LDL levels directly. It can also be determined whether the precipitation to remove VLDL and chylomicrons is further precipitating LDL. Methods of immobilizing precipitation reagents on a polymeric substrate are described in co-owned U.S. Patent Application Publication No. 2003/0224471, hereby incorporated by reference. In general, however, the precipitation reagents can be simply applied in solution and dried onto the strip for preparation of the precipitation element.

"A body-fluid sample" refers to an amount of fluid from an animal, such as a mammal, from which a determination of lipoprotein levels is sought. The body fluid is generally blood, serum, plasma, or a standard fraction, thereof. The body-fluid sample may contain an anticoagulant.

A "sample well" refers generally to a sample-receiving region, which may include a sample-receiving reservoir or pad, or a port through which sample is introduced into the device, e.g., into microchannel regions of a microfluidics device.

The term "selectively remove" one or more given cholesterol-containing lipoprotein means to preferentially remove the one or more given components relative to one or more other lipoprotein components contained in the same sample.

II. Assay Device

Figure 1B:
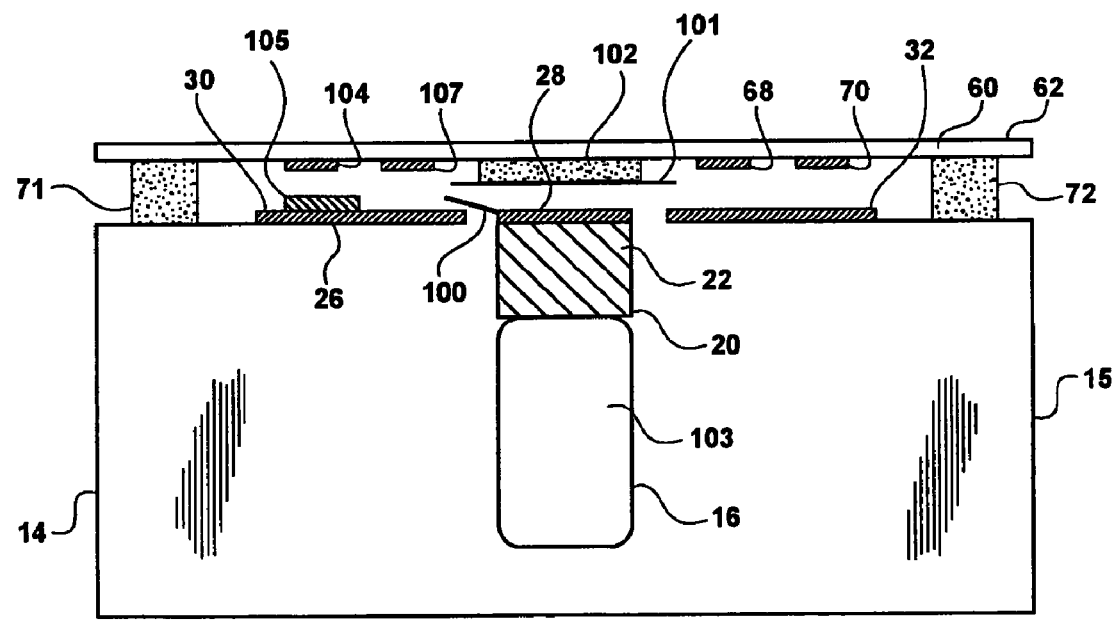
Figure 1C:
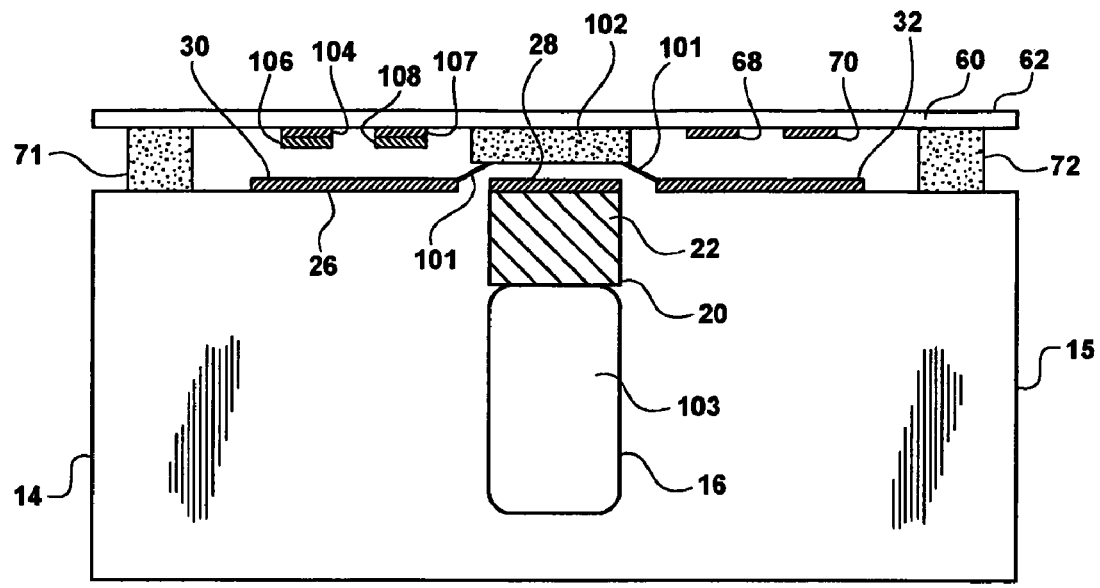
Figure 1D:
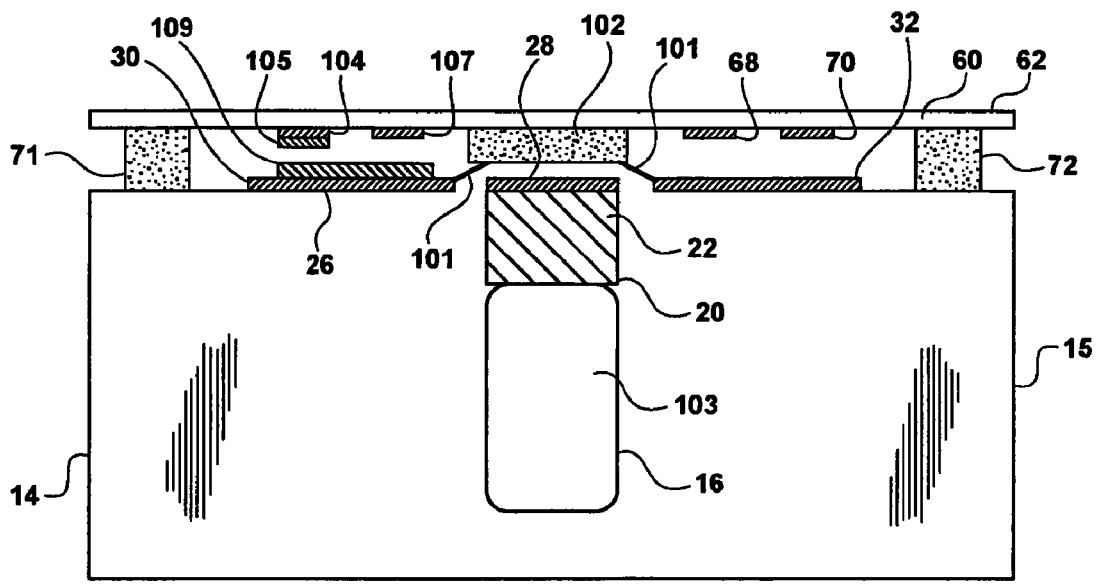
Figure 1E:
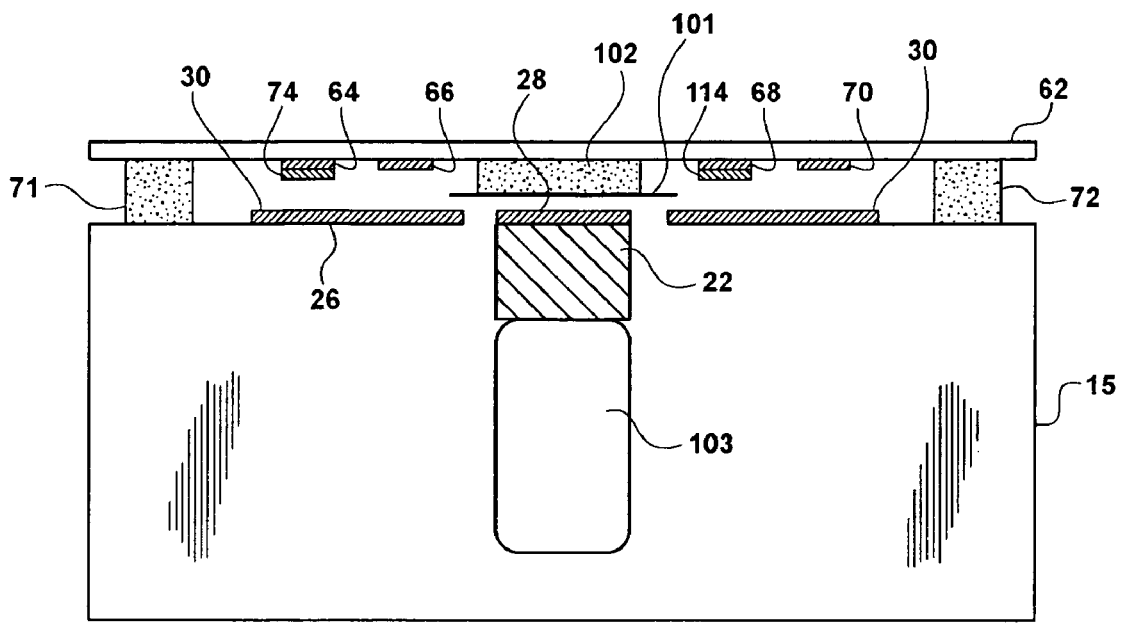
Figure 1F:
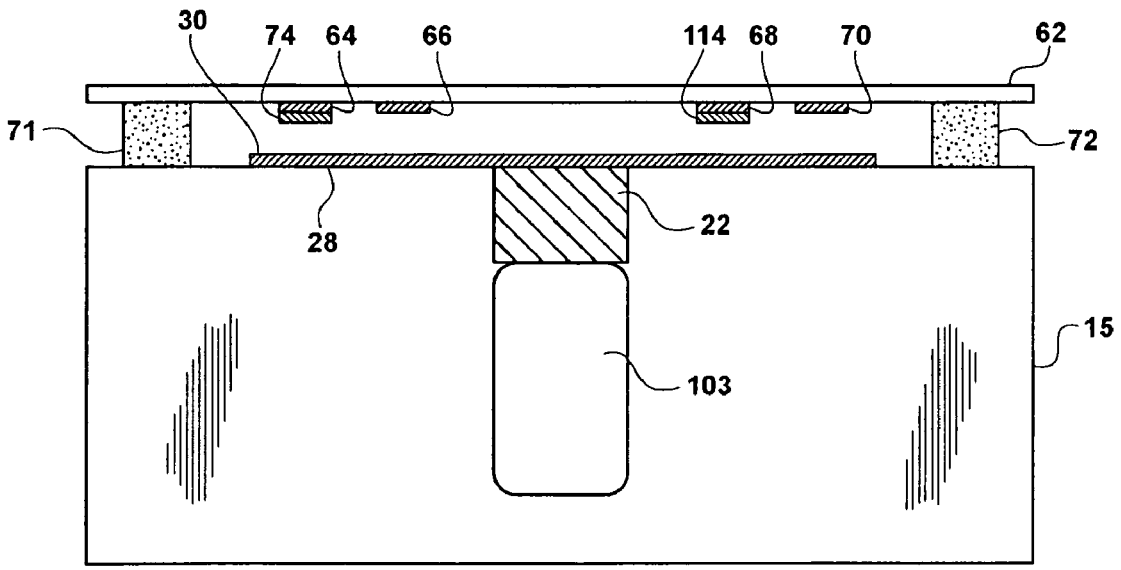
Figure 2:
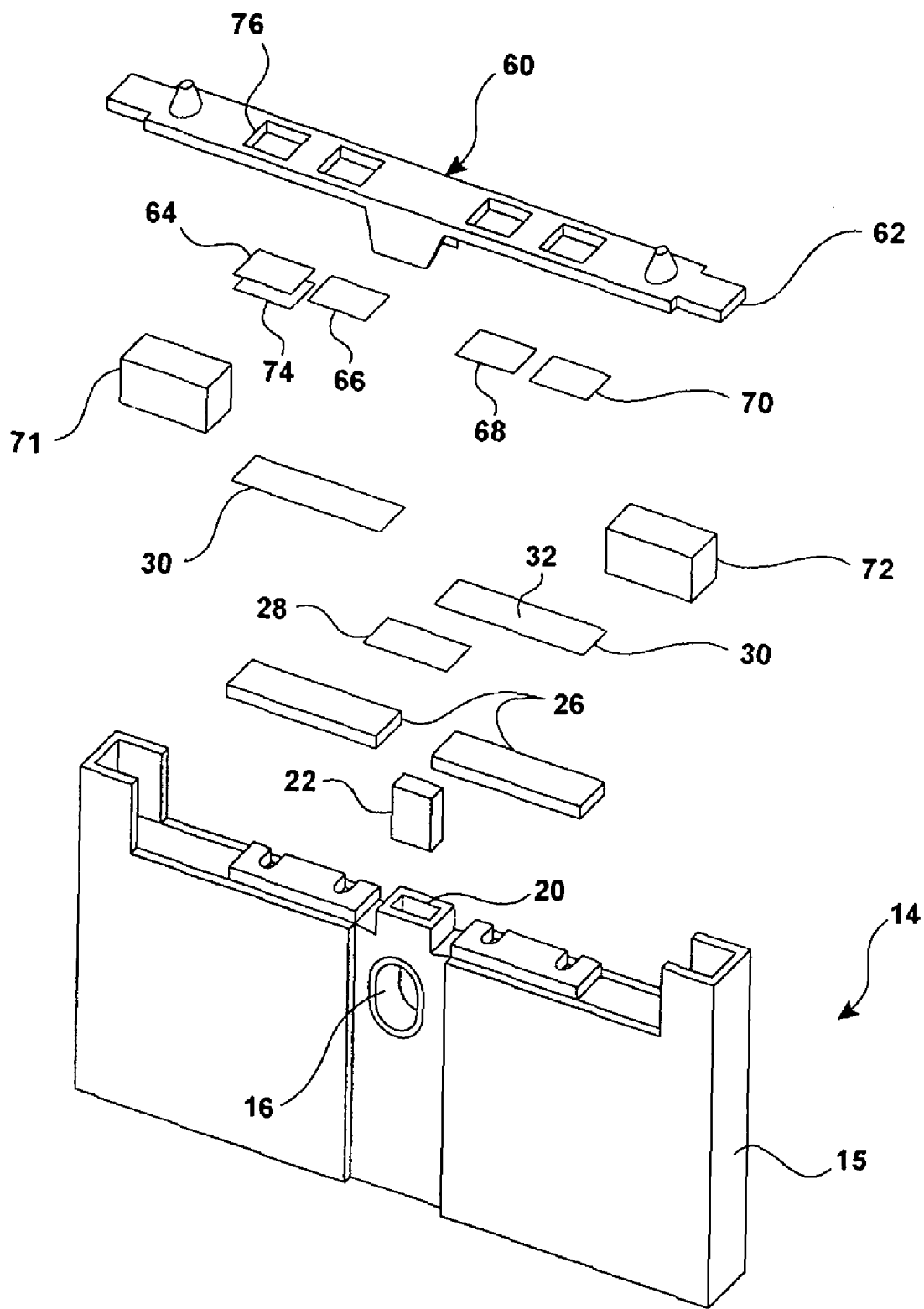
FIG. 2 is a perspective view, in exploded form, of a cassette device in accordance with one embodiment of the device.

FIGS. 1A-1F and 2 illustrate various cassette embodiments of the assay device 14 for determining the amount of LDL-associated cholesterol (LDL-C) in a body-fluid sample. FIGS. 1A-1F show side views of cassette devices. FIG. 2 is an exploded view of a cassette device. The cassette device is designed for determining LDL-C based on measured values for combinations of HDL-C and adjusted cholesterol or TCm (HDL plus LDL) in a small volume (typically between 10-50 µl) of a body-fluid sample, for example, whole blood, serum, plasma, or similar samples. In some embodiments, total cholesterol (TC) and/or triglycerides (TG) measurements may be used in combination with HDL-C and TCm. In further embodiments, TC may be used in the place of TCm in the determination.

As illustrated in FIGS. 1A-1F, the assay cassette 14 includes a cassette body 15 which defines a sample-receiving well 16 or 103 dimensioned and sized to receive a quantity of a body-fluid sample, typically between about 25-50 µl. The well 16 or 103 is in fluid contact with a sieving pad 22, which may be carried, e.g., in a notched region 20 formed in the upper edge of the cassette body 15. The fluid contact between the well 16 or 103 and the sieving pad 22 may be direct (as in FIG. 1B), or via a capillary conduit 18, e.g., formed in the plate at the base of the well (as in FIG. 1A). The fluid path from the sample well 16 or 103 to the reagent pads (or detection zones), are known as flow pathways, or flowpaths. In some embodiments, the cassette body 15 is a plastic plate, with the well, notched region, and/or capillary formed by standard molding or machining methods, although it will be appreciated that other suitable materials may be used.

The sieving pad 22 at least functions to partially remove (i.e., filter) large particulate matter (including blood cells) as the sample migrates through the pad matrix in a bottom-to-top direction. In some embodiments, the sieving pad 22 is formed of a glass fibrous matrix of material designed to draw aqueous fluid by surface wetting, and to retard the movement of blood cells as the blood sample is drawn through the matrix. That is, the pad serves as a chromatographic medium for separating cell-size particles from soluble serum components on the basis of different migration rates through the medium. One exemplary pad is a glass fiber filter, such as a GF/D or PD008 filter supplied by Whatman, having a packing density of about $0.16 g/cm^2$. The pad is cut to side dimensions of about 3×8 mm, and a thickness of about 1 mm. In some embodiments, the pad is dimensioned to absorb a defined volume of sample fluid, such as between about 15-25 μl. The sieving pad 22 may additionally contain red blood cell capture reagents, such as lectins, antibodies specific for red blood cell surface membrane proteins, thrombin, or ion exchange agents.

Figure 3:
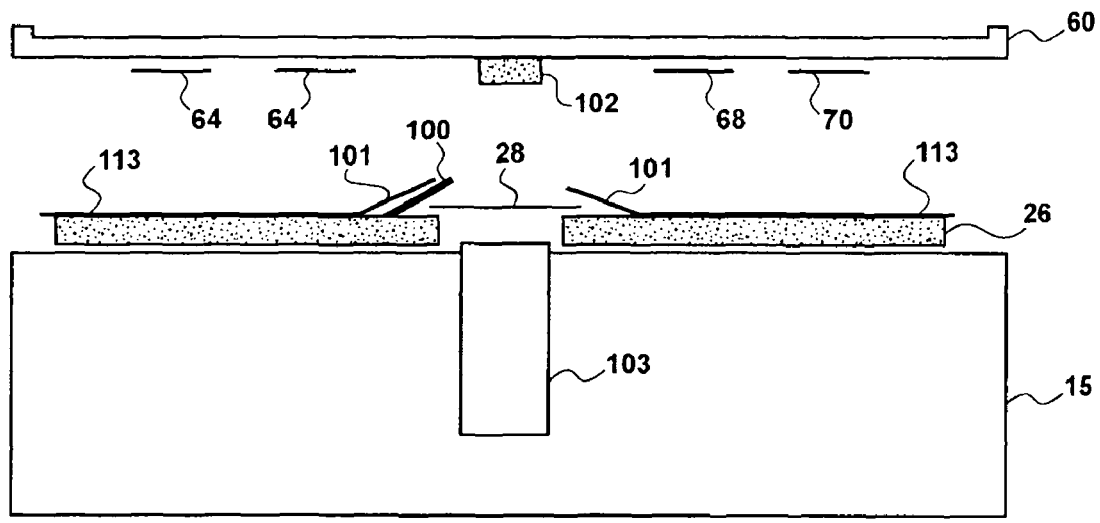
FIG. 3 is a side view illustrating an embodiment of the cassette device for determining LDL-C using a modified beta-quantititation method.
Figure 5:
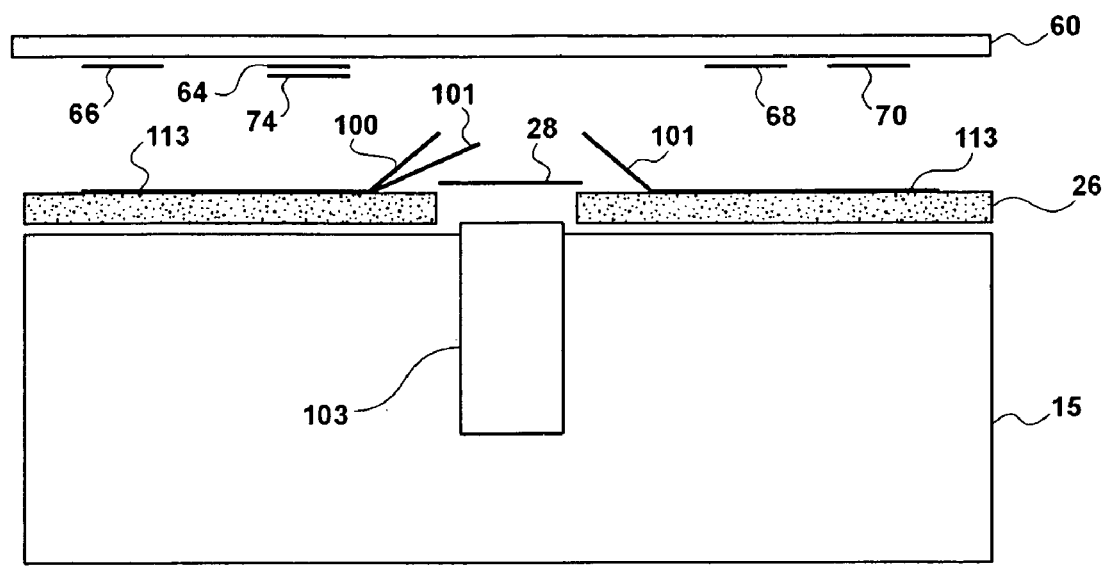
FIG. 5 is a side view illustrating a TCm embodiment of the cassette device for determining LDL-C using a modified beta-quantititation method or the Friedewald equation.

The sieving pad 22 is optionally adjacent to a central sample-application region 28, which is in proximity to one or more elongate strips or spreading layer(s) 30 which extend along the upper edge of the cassette body 15. The spreading layer 30 may have a first arm and a second arm, providing separate fluid pathways in the cassette body 15. The spreading layer 30 may be supported by, e.g., foam cushions 26, or other supports, as also shown in FIG. 2. The spreading layer 30 serves to distribute sample fluid from a central sample-application region 28 to sample-collection regions (exemplified by 32) of the spreading layer. As seen in FIGS. 3 and 5, the spreading layer 113 may be a wicking glass.

As shown in FIGS. 1A and 1B, the arms of the spreading layer 30 are in fluid contact with one or more flaps 101 of sufficient length to bridge the gap between the spreading layer 30 and the sieving pad 22 (or central sample-application region 28), thereby placing the spreading layer 30 and sieving pad 22 in fluid communication. These flaps 101 are thereby adapted for transferring a body-fluid sample from the sample-receiving well 16 to the spreading layer(s) 30. In one embodiment, the flaps 101 are continuous with the spreading layer 30, e.g., made from a single strip of material. The flaps are biased toward not contacting the central sample-application region 28 (or sieving pad 22) directly, as shown in the FIGS. 1A, 1B, 3 and 6. The flaps are brought into contact with the central sample-application region 28 (or sieving pad 22) following contact with the actuator pad 102 affixed to the support bar 62 (see below).

The flaps 101 may contain reagents for contacting the body-fluid sample in its flow pathway to the spreading layers. In some embodiments, the flaps 101 contain precipitation reagents for precipitating lipoprotein fractions, such as VLDL and chylomicrons or LDL, and may be referred to as precipitation flaps. Some of these reagents are described herein. In other embodiments, one or more additional flaps 100 are added, which may also or instead contain reagents, including precipitation reagents, and therefore be referred to as a precipitation flap. This additional flap 100 mediates fluid communication between the sieving pad 22 and spreading layers 30. While the figures show a separate flap 101 adapted for transferring a body-fluid sample from the sample-receiving well and additional flap 101 containing precipitation agents, it will be appreciated that a single flap may perform both functions. In another embodiment, the flap or flaps 100, 101 may be affixed to the actuator pad 102, e.g., as shown in FIG. 1B. In yet another embodiment, one of the flaps may be affixed to the actuator pad 102 and one of the flaps may be affixed to the spreading layer(s) 30. In a further embodiment, e.g., as seen in FIG. 1E, flap 101 is affixed to the actuator pad 102 and has sufficient length to bridge the gap between the spreading layers 30 and the sieving pad 22 (or central sample-application region 28), thereby placing the spreading layers 30 and sieving pad 22 in fluid communication. In this embodiment, the flap is biased toward not contacting the central sample-application region 28 (or sieving pad 22) directly. Flap 101 is brought into contact with the central sample-application region 28 (or sieving pad 22) following movement of the reaction bar 60 to bring the flap 101 into contact with the spreading layers 30 and the central sample application region 28 (or sieving pad 22). The skilled artisan will recognize other arrangement of the flaps that fall within the description.

The assay cassette 14 also includes a reaction bar 60 composed of an elongate support bar 62, and one or multiple wettable assay elements, reaction pads, or detection zones. In some embodiments, detection zones one, two, three, and four correspond to reaction pads 64, 66, 68, and 70, respectively. These pads are carried on the lower surface of the support bar 60, as shown. It will be appreciated that any number of reaction pads may be used. In some embodiments, the support bar 62 is transparent or has windows, e.g., window 76, as shown in FIG. 2, which may simply be openings in the support bar, which allow the reagent pads to be viewed through the support. The assay elements in the reaction bar can be attached to the support bar by a transparent or translucent adhesive material, by sonic welding, or other suitable bonding methods. Each reagent pad used in a particular assay contains analyte-dependent reagents effective to produce an analyte-dependent change in the pad which can be detected optically, either visually or by a detector, or via a biosensor, as described further below. All or any integral subset of the pads may be employed in a particular assay.

In some embodiments, the reagent pads are porous polymer membranes, typically having a thickness of about 100-150 μm and side dimensions of about 3 mm, for example. In some instances, the absorption volume of each element is between about 0.5-1.0 μl. In one embodiment, the assay elements, and in particular that used for HDL assay, are asymmetric membranes; that is, membranes having a porosity gradient across the thickness of the membrane, as described further below. The assay elements may also comprise a biosensor, as described below.

Movement of the support bar 62 from a first position (as shown in FIGS. 1A and 1B, for example) to a second position is effective to transfer sample fluid from the sample-receiving well 16 to the spreading layer(s) 30. Movement of the bar from its second to a third position is effective to transfer sample fluid from the spreading layer(s) 30 to the reaction pads 64, 66, 68, 70. These reaction pads are also called the first, second, third and fourth detection zones, respectively. In the first position, the support bar 62 is positioned such that the flaps 100, 101 do not contact the central sample-application region 28 (or sieving pad 22, directly), nor do the reagent pads 64, 66, 68, 70 contact the spreading layer(s) 30 (note that the flaps may contact the central sample-application region/sieving pad in this first position; however, fluid movement will begin with sample addition, rather than following the movement of the support bar).

In the second position, the support bar 62 is positioned such that the flaps 100, 101 contact the central sample-application region 28 (or sieving pad 22) directly allowing the sample to flow into the spreading layer(s) 30; however, the reagent pads (or detection zones) 64, 66, 68, 70 do not contact the spreading layer(s) 30.

In the third position, the reagent pads 64, 66, 68, 70 contact the spreading layer(s) 30. The position of flap 100, 101 are largely irrelevant at this stage of the assay, since the spreading layers are already wetted with sample and the detection of cholesterol (or TG) generally requires only a few minutes once the reagent pads 64, 66, 68, 70 are in contact with the spreading layer(s) 30.

Contact between the reagent pads and the spreading layer(s) may be broken after a desired amount of sample has entered the reaction pads, and/or after a determined contact time. Transferring can be controlled by monitoring the reflectance at the top surface of the assay element, which reflects extent of wetting, as described in co-owned U.S. Pat. No. 5,114,350. Alternatively, when the absorption capacity and rate of sample uptake of the wettable materials are known, the quantity of sample can be controlled with sufficient accuracy simply by using a predetermined contact time.

The mounting means can include, for example, a pair of resilient members, such as elastomeric or foam blocks 71, 72, which act to bias the reagent pads 64, 66, 68, 70 toward a non-transfer position i.e., the first and second positions, described, above, wherein the reagent pads (detection zones) 64, 66, 68, 70 are spaced apart from the spreading layer(s) 30, with a spacing typically of between about 0.5 to 1.0 mm. By compression or release of the resilient members 71, 72, contact between the spreading layer 30 and reagent pads can be selectively established and separated. The support blocks could be compressed by means of springs or a piston-like action. It will be appreciate that the support blocks may be made of any appropriate foam. Alternatively, external mechanical devices could engage the cassette body 15 and/or support bar 62 and move one towards the other. Such devices may include conventional components such as clamps, pistons, stepper motors, worm gears, or the like. An exemplary system is the CHOLESTECH LDX® Analyzer, a self-contained, automated analyzer advantageous for use with assay devices such as described herein.

In some embodiments, at least one of the reagent pads used for assaying HDL, has affixed thereto an additional membrane or pad containing a second precipitating agent 74 for precipitating non-HDLs in the body-fluid sample. The pad containing a second precipitating reagent 74 may be supported in a substantially coplanar position with respect to the other reagent pads (i.e., 66, 68, 70, or may be compressible such that the reagent pads (including those affixed to a second precipitation reagent-containing pad) all contact the spreading layer (or the arms of the spreading layer) at substantially the same support bar 62 position. In some embodiments, the second precipitation reagent pad 74 has a thickness of about 100-150 μm, side dimensions of about 3 mm, and an absorption volume of about 0.5-1.0 μl.

The second precipitation reagent pad 74 (or "second pad") may be affixed or adjacent to the reagent pad 64 for HDL measurement as in FIG. 1A, or affixed or adjacent to the spreading layer, as shown in FIG. 1B. The second reagent pad 74 contains a reagent for selectively precipitating non-HDLs. Such reagents are known in the art as precipitating reagents; see, e.g., a review by P S Bachorik et al., Methods in Enzymology 78-100 (1986). They include polyanionic compounds, such as sulfonated polysaccharides, heparin, or phosphotungstate, in the presence of a group-II cation, such as $Mg^{2+}$, $Mn^{2+}$, and $Ca^{2+}$. In exemplary embodiments, the reagent is a sulfonated polysaccharide, such as dextran sulfate, having a typical molecular weight of 50,000 to 500,000 daltons, in combination with magnesium acetate or chloride, buffered to maintain neutral pH.

The second precipitation reagent pad 74 is effective to entrap bound or precipitated non-HDL lipoproteins (e.g., LDL) within the reagent pad and prevent them from entering HDL assay element 64. While a glass fiber filter can be used for such a purpose, such glass fibers should be coated to prevent binding HDL in the presence of the reagents, as described in U.S. Pat. No. 5,451,370, cited above. In one embodiment, the second pad 74 is composed of a porous polymeric membrane, as described further below.

In some embodiments, the second precipitation reagents are immobilized to the second pad 74. In some embodiments, the negatively charged reagent, e.g., dextran sulfate, is immobilized by electrostatic forces and/or covalently to a membrane having positively charged surface groups. An exemplary material for this purpose is a nylon membrane having surface quaternary ammonium groups, such as the AM080 membrane provided by Cuno Corp. (Meridian, Conn.). In this case, the membrane acts as an affinity separation medium, such that non-HDL lipoproteins bind to the second precipitation reagents affixed to the membrane, rather than precipitating, and are thereby separated from the sample fluid.

Other commercial polymeric membranes having a cationic surface include Immobilon-Ny+™ (Millipore Corp., Bedford, Mass.), Zetabind® (also from Cuno Corp.), GeneScreen® (NEN/DuPont, Boston, Mass.), Hybond N+ (Amersham, Piscataway, N.J.) and Posidyne® (Pall Corp., Glen Cove, N.Y.). U.S. Pat. No. 5,543,054 (Charkoudian et al.) describes a method for covalently binding negatively charged carbohydrates to a membrane having reactive moieties in proximity to positively charged moieties on its surface. The membrane is, for example, a porous polymer, e.g., polytetrafluroethylene, polyvinylidene fluoride, polyester, polyamide, polycarbonate, polypropylene, polymethylmethacrylate, polymethacrylate, polysulfone, or polystyrene, coated with Hercules R-4308TM. a polyamido-polyamine epichlorohydrin resin.

In one embodiment, the second precipitation reagent pad 74 is composed of an asymmetric membrane; that is, a membrane having a pore size gradient across its thickness. In some embodiments, the an asymmetric membrane is used with precipitating reagents incorporated into the membrane in soluble form, for optimum entrapment of precipitate, e.g., dextran sulfate and a magnesium salt, such as magnesium acetate. An exemplary procedure for preparing such membranes for incorporation into the device is described in Example 1. In this case, the soluble second precipitation reagents are released into the sample solution as it penetrates the membrane. The preparation of asymmetric membranes is described, for example, in U.S. Pat. Nos. 4,629,563, 5,171,445, 5,886,059, 5,536,408, 5,562,826, and 4,774,192; in D. R. Lloyd, "Materials Science of Synthetic Membranes", ACS Symposium 269: 1-21 (1985). Such asymmetric membranes are commercially available in a variety of pore sizes and pore-size ratios. Materials of fabrication include polysulfones, polyethersulfones, polyamides, polyether amides, polyurethanes, cellulose acetate, polyvinyl pyrrolidone, polystyrenes and modified polystyrenes, as well as blends, copolymers, and laminar composites. An exemplary asymmetric membrane is a polysulfone or polyethersulfone membrane, such as membranes provided by Pall Corporation. Minimum pore sizes typically range from 0.01 to 1.0 μm, with maximum/minimum pore size ratios up to 100 or more. Thickness is typically 100-150 μm.

The asymmetric membrane may be oriented with its larger pored surface facing the sample application region; that is, facing downward as in FIGS. 1A, 1B, and 2, and its smaller pored surface facing, and (in some embodiments) contacting, an assay element, e.g., reagent pads 64, containing reagents for detecting HDL, as described further below. This orientation allows free access of sample into the pad through the larger pores, and prevents passage of precipitated material, formed as the solution contacts soluble precipitating agent, through the smaller pores, which are generally 1 μm or less in diameter. This pore size is also typical for non-asymmetric membranes.

In one embodiment, second precipitation reagent pad 74 consists of a single membrane. The use of multiple stacked membranes, i.e. up to about six, where at least one and (in some embodiments) each membrane contains reagents for binding or precipitation of non-HDL lipoproteins, for second precipitation reagent pad 74 is also contemplated. They may contain immobilized reagent, as described above, or they may be impregnated with soluble reagent. In the latter case, asymmetric membranes are typically used, and may be oriented such that the smaller pored surface of the uppermost membrane faces assay reagent pad 64, and the larger pored surface of the lowest membrane faces the sample application region.

In one embodiment, reagent pad 64 is also a polymeric membrane, containing reagents for detecting HDL and may be an asymmetric membrane as described above. In order to present the more uniform surface for optical scanning and quantitation of assay results, an asymmetric membrane employed for reagent pad 64 is oriented with its smaller pored surface facing upward, and its larger pored surface facing the second precipitation reagent pad 74. Alternatively, an asymmetric membrane employed for reagent pad 64 may be oriented with its larger pored surface facing upward and its smaller pored surface facing second precipitation reagent pad 74. This orientation is more suitable for assays in which a visual, qualitative reading is to be made from the upper surface.

If desired, HDL assay reagents, such as peroxidase, may be immobilized to the reaction pad 64, according to well known methods for enzyme immobilization (see, e.g., U.S. Pat. Nos. 4,999,287; 5,419,902; Blum, L. J. et al., Anal. Lett. 20(2): 317-26 (1987); Kiang, S. W. et al., Clin. Chem. 22(8):1378-82(1976); Guilbault, G. G., Ed., Modern Monographs in Analytical Chemistry, Vol. 2: Analytical Uses of Immobilized Enzymes (1984); Torchilin, V. P., Progress in Clinical Biochemistry and Medicine, Vol. 11: Immobilized Enzymes in Medicine (1991)). In another embodiment, a reagent, such as catalase, which is effective to decompose any generated hydrogen peroxide that might diffuse downward from reagent pad 64, may be included in the second precipitation reagent pad 74.

In one embodiment, where two attached polymeric membranes are employed for reagent pad 64 and second precipitation reagent pad 74, respectively, the appropriate reagents are impregnated or immobilized, and the membranes are processed as a two-membrane layer for incorporation into the assay device during manufacture.

In some embodiments, as seen in FIGS. 1E-1F, at least one of the reagent pads used for assaying TCm, has affixed thereto an additional membrane or pad 114 containing an agent for precipitating VLDL and chylomicrons in the body-fluid sample. In this embodiment, it will be appreciated that the TCm and HDL reagent pad may be any of the first, second, third (where included) or fourth (where included) detection zones. In the embodiment shown in FIGS. 1E-1F, the TCm reagent pad 68 is the third detection zone. The pad containing the precipitating reagent 114 may be supported in a substantially coplanar position with respect to the other reagent pads (i.e., 64, 66, 68, 70), or may be compressible such that the reagent pads (including those affixed to a second precipitation reagent-containing pad) all contact the spreading layer (or the arms of the spreading layer) at substantially the same support bar 62 position. In some embodiments, precipitation reagent pad 114 has a thickness of about 100-150 μm, side dimensions of about 3 mm, and an absorption volume of about 0.5-1.0 μl.

The precipitation reagent pad 114 (or "precipitation pad") may be affixed or adjacent to the reagent pad 68 for TCm measurement as in FIGS. 1E-1F. In other embodiments, the precipitation pad may be affixed or adjacent to the spreading layer. The precipitation pad 114 contains a reagent for selectively precipitating VLDL and chylomicrons as described above.

The precipitation pad 114 is effective to entrap bound or precipitated VLDL lipoproteins and/or chylomicrons within the precipitation pad and prevent them from entering the TCm assay element 68. It will be appreciated that in the embodiment including a precipitation pad 114, the flaps 100, 101 may or may not additionally include reagents for selectively precipitating VLDLs and chylomicrons. It will be appreciated that the flap may be optional where the reagents for precipitating VLDL and chylomicrons are included in a precipitation pad 114. As seen in FIG. 1F, the spreading layer 28 extends along the upper edge of the cassette body 15 and is in contact with the sieving pad 22 and sample receiving well 16 or 103. It will be appreciated that spreading layer 28 may be formed of one or more elongate strips and may be in proximity to one or more elongate strips or spreading layer(s) 30. In one embodiment, the precipitation pad 114 is composed of a porous polymeric membrane, as described above with reference to the second precipitation reagent pad 74.

In one embodiment, precipitation pad 114 consists of a single membrane. The use of multiple stacked membranes, i.e. up to about six, where at least one and (in some embodiments) each membrane contains reagents for binding or precipitation of VLDL and/or chylomicrons is also contemplated. The precipitation pad(s) 114 may contain immobilized reagent, as described above, or may be impregnated with soluble reagent. In the latter case, asymmetric membranes are typically used, and may be oriented such that the smaller pored surface of the uppermost membrane faces assay reagent pad 68, and the larger pored surface of the lowest membrane faces the sample application region.

In one embodiment, reagent pad 68 is also a polymeric membrane, containing reagents for detecting total cholesterol and may be an asymmetric membrane as described above. In order to present the more uniform surface for optical scanning and quantitation of assay results, an asymmetric membrane employed for reagent pad 68 is oriented with its smaller pored surface facing upward, and its larger pored surface facing the precipitation pad 114. Alternatively, an asymmetric membrane employed for reagent pad 68 may be oriented with its larger pored surface facing upward and its smaller pored surface facing precipitation pad 114. This orientation is more suitable for assays in which a visual, qualitative reading is to be made from the upper surface.

In a further embodiment, at least one of the HDL, TCm, TC, and/or the TG assay element(s) comprises a biosensor, as described, for example, in PCT WO 9958966 (Dobson et al.), which is incorporated herein by reference. This document discloses a microscale biosensor device, comprising a conducting surface, a layer of dielectric material overlying the conducting surface, and a plurality of pores extending through the dielectric layer. Each of the pores can act as a microelectrode, converting a chemical response into an electrical signal, by virtue of a biopolymer within the pore in contact with the conducting surface. In use, a fluid containing an analyte to be assayed is applied to the pores so as to be in contact with the biopolymer. For example, for the detection zone for measuring HDL, this can be achieved by placing the second precipitation reagent pad 74 in fluid contact with the HDL reagent pad 64; that is, the pore-containing surface of the biosensor.

A counter electrode is provided which is in electrical contact with the conducting surface via the sample fluid. A voltage is applied between the counter electrode and the conducting surface, and the current that flows there between is measured. The measured current is indicative of the amount of a chosen analyte in the assayed fluid.

The microelectrodes may function as amperometric biosensors. Briefly, an amperometric biosensor functions by the production of a current when a potential is applied between two electrodes. An example is the Clark oxygen electrode, which measures current produced by reduction of oxygen or oxidation of hydrogen peroxide.

The dependence of such biosensors on dissolved oxygen concentration can be overcome by the use of 'mediators', which transfer the electrons directly to the electrode, bypassing the reduction of the oxygen co-substrate. Ferrocenes represent a commonly used family of mediators.

The biopolymer within the microelectrode pores is typically an enzyme, such as, for the measurement of HDL-associated cholesterol, cholesterol oxidase. Cholesterol is oxidized by cholesterol oxidase to the corresponding ketone, liberating hydrogen peroxide, which can then be converted to water and oxygen by the enzyme peroxidase. Either oxygen or hydrogen peroxidase is then measured electrochemically at the biosensor. It will be appreciated that one, some or all of the detection zones may include a biosensor.

III. Assay Method

In operation, a body-fluid sample is placed into the well 16 or 103, and is imbibed by capillary action through the sieving matrix 22, where large particulates, including red blood cells, are removed (i.e., filtered), and thence into the spreading layer(s) 30. These steps take place while the device is in the first position or the second position, when the actuator pad 102 contacts the flaps 101 and presses them against the central sample-application region 28 or sieving pad 22, directly. In the embodiment shown in FIG. 1E, flap 101 is in contact with the sample-application region 28 or sieving pad 22 in the second position. In the second position, the reaction pads (or detection zones) 64, 66, 68, 70 are not in contact with the spreading layer(s) 30.

After a desired amount of the body-fluid sample has been transferred to the various sample-collection regions of the spreading layer(s) 30, the device is moved to the third position, typically by moving support bar 60, to place reaction pads 64, 66, 68, 70 in contact with the spreading layer. In the case where the HDL reagent pad 64 is affixed to a second precipitation reagent pad 74, and/or where the TCm reagent pad 68 is affixed to the precipitation pad 114, it is the second precipitation reagent pad 74 and/or precipitation pad 114, along with reagent pads 66 and 70, which contact the spreading layer arms. Similarly, in the case where the TCm reagent pad 68 is affixed to a precipitation pad 114, it is the precipitation pad 114 which contacts the spreading layer 30. In this third position, sample fluid in the well 16 or 103 is drawn into each contacted reagent pad by capillary flow/action, with fluid movement occurring in a direction normal to the pad surfaces. The cassette device 14 is maintained in this position until a desired degree of wetting of the reagent pads is achieved, or a predetermined time period. The cassette body 15 or support bar 62 is then moved or released, if desired, to break contact between the reagent pads and spreading layer 30, when a desired amount of sample fluid has entered the reagent pads, and/or after an appropriate contact time, e.g., as described in Example 2 below.

In embodiments of the device in which a second precipitation reagent pad 74 is present but not affixed to reagent pad 64, respective movement of the support bar 62 and cassette body 15 toward each other, typically by moving the support bar downward, first places reagent pad 64 in contact with second precipitation reagent pad 74, to approximate the arrangement of elements shown in the figures. Contact is maintained until a desired degree of wetting is achieved or a predetermined time period, as described above.

Sample entering the second precipitation reagent pad 74 contacts precipitating or binding reagent contained in the membrane, such that non-HDL lipoproteins (e.g., LDL) is selectively precipitated and retained by filtration, in the case of soluble reagents, or bound to the membrane, in the case of immobilized reagents. The membrane is thus effective to entrap non-HDL lipoproteins, while allowing passage of serum containing liquid-phase HDL to the HDL reagent pad 64. The HDL reagent pad contains reagents for quantification of HDL-associated cholesterol. In some embodiments, these include cholesterol esterase, for releasing free cholesterol from HDL; cholesterol oxidase, for producing $H_2O_2$ by reaction with free cholesterol; peroxidase, which converts $H_2O_2$ to oxygen and water; and a coupled dye system which is converted, in the presence of peroxidase and $H_2O_2$, to a distinctively colored signal reaction product. Alternatively, the generated oxygen or $H_2O_2$ may be measured by the use of a biosensor, as described above.

During operation, as sample fluid passes through the HDL assay path, comprising reagent pad 64 and second precipitation second pad 74, its leading edge passes in an upward direction through second precipitation reagent pad 74, where non-HDL lipoproteins are entrapped, to reagent pad 64, where HDL reacts with the assay reagents therein, for measurement of HDL-associated cholesterol. Flow continues in this manner until the absorption capacity of the reagent pad is reached. Accordingly, quantification of HDL-associated cholesterol in reagent pad 64 occurs concurrently with the precipitation or binding reaction taking place in second precipitation reagent pad 74. In some embodiments, the volume of sample fluid transferred to the HDL assay path is equal to or greater than the absorption capacity of reagent pad 64, and less than or equal to the combined absorption capacity of reagent pad 64 and second precipitation reagent pad 74.

One advantage of arranging the second precipitation reagent pad upstream and in juxtaposition to the HDL reagent pad is that the sample distribution path does not contain non-HDL precipitating or binding reagents. Such reagents are present only in second precipitation reagent pad 74. Therefore, the possibility of interference from these second precipitation reagents (e.g., in assays of analytes other than HDL) is eliminated.

In a further embodiment, the central sample-application region is in contact with the spreading layer(s) in a first position. The central sample-application region is in contact with the reaction pads (or detection zones 64, 66, 68, and 70 in a second position.

In some embodiments, each of the reaction pads contain reagents for producing $H_2O_2$ via reaction of the lipoprotein analyte with an enzyme; the $H_2O_2$ subsequently converts a substrate reagent to a colored signal reaction product, or is measured electrochemically, as described above. Such reagents include, for example, peroxidase and a coupled dye system which is converted by the peroxidase, in the presence of $H_2O_2$, to a distinctively colored signal reaction product. Enzymatic color reactions which employ a variety of substrate-specific oxidases, for enzymatic generation of $H_2O_2$, and subsequent oxidation of a dye to form a colored reaction product, are well known.

In a related embodiment of the apparatus and method additionally measure triglycerides (TG) in a body-fluid sample. Measuring TG permits the use of the Friedewald equation, i.e., LDL-C=TC−HDL-C−(TG/5). The Friedewald equation is comparable to the beta-quantitation method for measuring LDL-C, except where the samples contain high levels of TG. Reagents for detecting TG include, but are not limited to, lipase, L-glycerol kinase, and L-glycerol-3-phosphate oxidase, for generating $H_2O_2$ from triglyceride, via the intermediate L-glycerol-3-phosphate. In an embodiment, the apparatus may be used to measure TG. Where the TG is below about 250 mg/dl, either the beta-quantification equation (LDL-C=TCm−HDL) or the Friedewald equation (LDL-C=TC−HDL-C−(TG/5)) may be used. Where the TG is above about 250 mg/dl, the beta-quantification equation is used.

The reference method for measuring LDL-associated cholesterol (LDL-C) in a sample that is used by the Centers for Disease Control (CDC) and recommended by the National Cholesterol Education Program (NCEP) involves a semi-direct, beta-quantitation method, which calculates LDL-C as the difference between the measured amount of total cholesterol (TCm) in the 1.006 kg/l density fraction and the measured amount of HDL-C, i.e., LDL-C=TCm−HDL-C. The 1.006 kg/l density fraction is obtained from ultracentrifugation of the serum fraction to remove chylomicrons and VLDL (Handbook of Lipoprotein, pp 225-26). HDL-C measurements are made following manganese/heparin precipitation of the TCm sample. While the Friedewald equation is useful for calculating LDL-C levels in fasting patients and/or patients with low to normal levels of TG, it is inherently error prone in non-fasting patients or patients with high TG levels (e.g., greater than about 400 mg/dl).

The present method, in one aspect, provides an apparatus and method for directly measuring LDL-C in a body-fluid sample, such as a blood sample, which may also contain HDL, VLDL, and/or chylomicrons. The measurement is performed entirely in flow strip format by passing the fluid sample through a sequence of porous elements having reagents for manipulating the fluid blood samples. Using the assay cassette device 14 described herein, VLDL and chylomicrons are removed by mild precipitation with precipitating agents, e.g., magnesium/dextran, eliminating the need for the cumbersome and time-consuming ultracentrifugation step used in the reference method.

Embodiments of the cassette device having at least two or more reaction pads can be used to simultaneously measure HDL-C and adjusted total cholesterol (TCm), which can then be used to calculate LDL-C based on the beta-quantitation equation (i.e., LDL-C=TCm−HDL-C; FIG. 3). Reaction pads for measuring HDL and TCm contain the above-described common pathway components (peroxidase and a coupled dye system) such that generated $H_2O_2$ can be measured or produces a distinctly colored signal reaction product. In such cases, the determination of LDL-C is independent of triglycerides (TG), which need not be measured. This embodiment is particularly well-suited for determining LDL-C in non-fasting patients, and/or patients with high TG levels, where the Friedewald equation (which takes into account TG levels) tends to be least accurate. This embodiment is described herein as the "LDX" version of the CDC method.

An embodiment of the cassette device having at least three or more reaction pads can be used to simultaneously measure HDL-C, total cholesterol (TC), and triglycerides (TG), which can then be used to calculate LDL-C using the Friedewald equation (i.e., LDL-C=TC−HDL-C−TG/5) is shown in FIG. 5. In this embodiment, the TC reagent pad is exposed to the body-fluid sample without prior exposure to a precipitating or binding reagent (i.e., TC=HDL+LDL+VLDL+chylomicrons) or with exposure to a first precipitating reagent for removing VLDL and chylomicrons (i.e., TCm=HDL+LDL), depending on the embodiment. This embodiment is particularly well-suited for determining LDL-C in fasting patients, and/or patients with low to normal TG levels, where the Friedewald equation tends to be most accurate.

The TG reagent pad includes one or more reagents for determining TG levels including, but not limited to, lipase, L-glycerol kinase, and L-glycerol-3-phosphate oxidase, for generating $H_2O_2$ from triglyceride, via the intermediate L-glycerol-3-phosphate. The serum sample drawn into the TG reagent pad is not exposed to precipitating or binding reagents, and thus contains all of the serum lipoproteins. The TG signal therefore represents total serum triglycerides. Reference standard pads may also be employed (see, for example, the system described in co-owned U.S. Pat. No. 5,114,350, which is incorporated herein by reference).

a. LDX Embodiment

In one embodiment, illustrated by FIG. 3, the sample-receiving well 103, contains the sample and first precipitation reagents, such as magnesium acetate and heparin and/or dextran sulfate, at sufficiently low concentration to selectively precipitate VLDL and chylomicrons but not LDL or HDL. In one embodiment, the concentration of magnesium acetate (or similar salt of a divalent cation) is from about 50 mM to about 600 mM. According to this embodiment, a TCm reagent pad contacts a spreading layer 113 wetted with the sample containing LDL and HDL (TCm) but depleted for VLDL and chylomicrons. The TCm measurement therefore corresponds to LDL+HDL.

Also according to this embodiment, a second precipitation reagent is used to precipitate LDL from the sample containing LDL and HDL, leaving essentially only HDL in the sample to contact the HDL reagent pad. The second precipitation reagent may be, e.g., magnesium acetate and dextran (or similar reagents), at sufficiently concentrations to selectively precipitate LDL but not HDL. In one embodiment, the concentration of magnesium acetate (or similar salt of a divalent cation) is from about 50 mM to about 500 mM and the concentration of dextran (or similar reagent) is from about 0.01% to about 0.5%. The second precipitation reagent may be provided in (or on) a flap (e.g., a dry-strip flap) 100, 101 adapted for transferring the body-fluid sample from the sample-receiving well 103 to the spreading layer 113. This "precipitation flap" may be the same flap 101 as used to transfer the body-fluid sample to the spreading layer(s) 113 or an additional flap 100, as shown in FIGS. 1A, 1B, 3, and 5. In this manner, the sample transferred to the spreading layer is depleted for LDL. In this embodiment, the TCm reagent pad 68 and the HDL reagent pad 64 should be arranged on different sides of the cassette device 14, for contacting the arm of the spreading layer in contact with the sample that has contacted the first precipitation reagent but not the second precipitation reagent. The HDL reagent pad 64 on the other side of the cassette device 14, for contacting the arm of the spreading layer in contact with the sample that has contacted the first precipitation reagent and the second precipitation reagent in the second precipitation reagent pad 74.

In a related embodiment, the second precipitation reagent is provided in a second precipitation reagent pad 74 adjacent to the HDL reagent pad 64, as also shown in FIGS. 1A and 1B. In this embodiment, the arms of the spreading layer 30 are wetted with the same sample (i.e., containing HDL and LDL but no VLDL or chylomicrons), therefore the HDL reagent pad and TCm (i.e., HDL+LDL) reagent pad, may be on the same side of the cassette device, on opposite sides, or both. In a related embodiment, the second precipitation reagent is included in the pad 106 adjacent to the spreading layer 30. The HDL reagent pad 104 and TC reaction pad 107 are indicated.

To establish proof of the TCm-HDL concept, Table 1 shows a comparison of LDL-C determinations obtained using the LDX embodiment described above with LDL-C determinations using a reference method. In the LDX embodiment, the second precipitation reagent was provided on an additional precipitation flap 100 adapted (in combination with flap 101) for transferring the body-fluid sample from the sample-receiving well 16 or 103 to the spreading layer 30. Collection day and donor number are shown in the first two columns.

TABLE 1

LDL-C determinations

| Day | Donor | HDL | TC - post PPT | TC – HDL | Friedewald calculated LDL |
|---|---|---|---|---|---|
| 1 | 5 | 52.7 | 165.9 | 113.1 | 110.7 |
| 2 | 1 | 33.7 | 198.5 | 164.8 | 151.7 |
| 2 | 2 | 49.9 | 191.9 | 142.0 | 166.4 |
| 2 | 4 | 9.0 | 64.9 | 55.9 | 57.3 |
| 2 | 7 | 61.1 | 184.3 | 123.2 | 135.4 |
| 3 | 2 | 48.8 | 92.8 | 43.9 | 34.6 |
| 3 | 6 | 62.4 | 192.4 | 130.0 | 145.5 |
| 3 | 7 | 49.2 | 164.2 | 115.0 | 104.0 |
| 3 | 8 | 60.8 | 210.8 | 150.0 | 151.5 |
| 4 | 1 | 41.4 | 132.2 | 90.8 | 83.9 |
| 4 | 3 | 48.6 | 182.0 | 133.4 | 138.8 |

Measured HDL-C and TCm are shown in columns 3 and 4, respectively, with the amount of LDL (i.e., TCm–HDL-C) calculated by subtraction in column 5. Column 6 shows the amount of LDL-C calculated using the Friedewald equation based on Beckman data for TC, TG and HDL-C.

Figure 4:
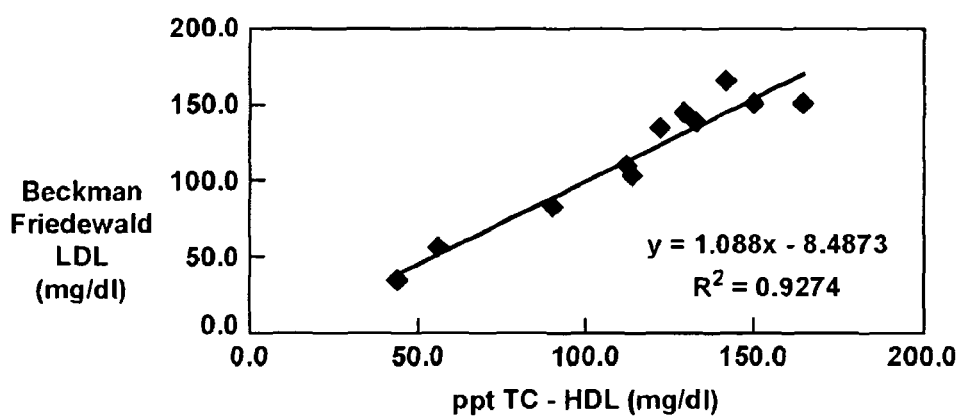
FIG. 4 is a graph showing the correlation of LDL-C determinations obtained using a LDX embodiment of the cassette device (x axis) with LDL-C determinations obtained using the Beckman "Friedewald" reference method (y axis) for eleven donors.

FIG. 4 is a graph showing the correlation between LDL-C determined using the LDX embodiment and LDL-C determined using the Friedewald equation. The graph is based on the data shown in Table 1. As seen in the graph, there is a strong correlation between the two LDL-C calculations, particularly at lower LDL-C levels. The $R^2$-value was about 0.927 and y=1.088x−8.4873. These results show that the LDX assay provides a rapid and efficient method for determining LDL-C levels, which have a strong correlation with levels obtained using conventional methods.

b. TC Embodiment

In another embodiment, the first precipitating reagents are provided in a precipitation flap (or dry strip flap) 100 (or 101) adapted for transferring the body-fluid sample from the sample-receiving well 16 or 103 to the spreading layer 30. The second precipitation reagent is provided in a second precipitation reagent pad 74, as in FIG. 5 (also FIGS. 1A and 1B). In this embodiment, one arm of the spreading layer is wetted with sample depleted for VLDL and chylomicrons following contact with the first precipitating reagents (e.g., manganese and heparin, referred to TCm reagents). The other arm of the sample containing all lipoproteins, i.e., HDL, LDL, VLDL, and chylomicrons.

In this arrangement, the HDL reagent pad 64 (which is adjacent to the second precipitation reagent pad 74) and the TCm reagent pad (e.g., 66 in FIGS. 1A and 1B) are typically arranged on one side of the cassette device, wherein the spreading layer 30 wets with a sample having contacted the first precipitating reagents in the precipitation flap 100. In this manner the first TCm reagent pad measures LDL+HDL, and can be used in combination with the measurement obtained from the HDL reagent pad to calculate LDL-C similar to the beta-quantitation method (as with the LDX embodiment). A TC reagent pad (e.g., 70 in FIGS. 1A and 1B) and a TG reagent pad (e.g., 68 in FIGS. 1A and 1B) are arranged on the opposite side of the cassette device 14, wherein the spreading layer 30 wets with the sample containing all lipoproteins. This embodiment is referred to herein as the "TC" embodiment.

In other embodiments, both the first and second precipitation reagents are provided on pads, without the need for a precipitation flap. Examples of this embodiment are shown in FIGS. 1C-1D. In the embodiment exemplified in FIG. 1C, the first precipitation reagents (for precipitating VLDL and chylomicrons) are provided in pad 108 adjacent to the TC reaction pad 107, and the second set of precipitation reagents (for precipitating VLDL, chylomicrons, and LDL) are contained in a second pad 106 which is adjacent to the HDL reaction pad 104. In this manner, the precipitation reagents are provided immediately upstream of the reagent pads. In the embodiment shown in FIG. 1D, the first precipitation reagents (for precipitating VLDL and chylomicrons) are provided in pad 109 carried on spreading layer 26, and second precipitating reagents for precipitating LDL are contained in a second pad 105 which is adjacent to the HDL reaction pad 104.

Alternatively, as seen in FIG. 1E, the first precipitation reagents (for precipitating VLDL and chylomicrons) are provided on a pad 114 attached to the TCm reagent pad 68. In this embodiment, flaps 100,101 may or not additionally include the first precipitation reagents. Where the flaps do not include the first precipitation reagents, the TC and TCm reagent pads may be on the same or opposite sides of the cassette. As seen in FIG. 1F, where the first precipitating reagents are included in a pad 114 attached to the TCm reagent pad 68, the flaps may be optional.

FIGS. 1G and 1H show embodiments of the present disclosure suited to a slide-based assay or a microfluidic assay. In this general embodiment, reaction regions 68, 70, 104, and 107 are in fluid contact with the sample well 103 via capillaries or channels 110 in the microfluidic device 111. The capillaries or channels 110 contain, e.g., as surface bound binding reagents, first reagent region 106 and/or 105. The HDL reaction area 104, TCm reaction area 107, TC reaction area 70, and TG reaction area 68 are indicated. The underlying chemistry is the same as for the embodiments, except that the precipitation agents may be surface-bound binding agents rather than precipitating salts, and the detection reagents may be contained in a reservoir, rather than in a dry-strip pad. In some embodiments, a single fluidic pathway, such as pathway 110, may connect each sample well to a corresponding reaction region, as shown in FIG. 1G. In this figure, the binding agents for VLDL and chylomicrons are shown at area 106, and binding agents for VLDL, chylomicrons and LDL are indicated at area 105. In other embodiments, the microfluidic connections between the sample well and reaction regions may be bifurcated, as in FIG. 1H.

Figure 6:
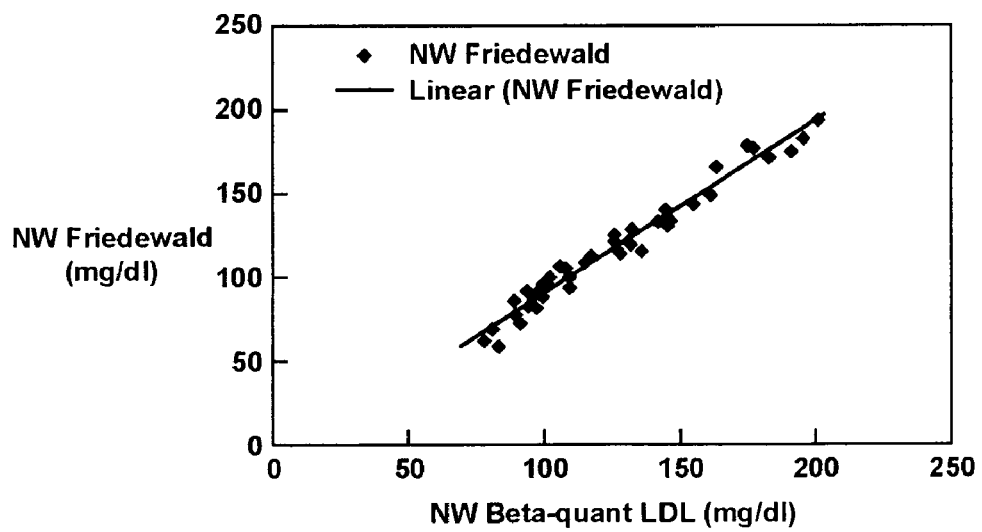
FIG. 6 is a graph showing the correlation of LDL-C determinations obtained using a TCm embodiment of the cassette device with LDL-C determinations obtained using the Friedewald equation. The levels of TG in the samples are from about 43 to about 280 mg/dl.
Figure 7:
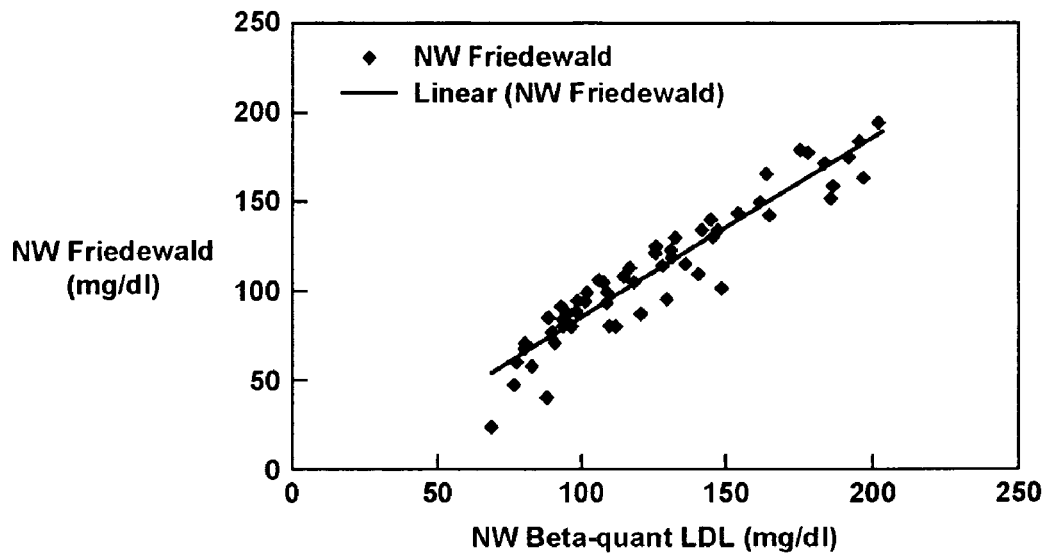
FIG. 7 is a graph showing the correlation of LDL-C determinations obtained using a TCm embodiment of the cassette device with LDL-C determinations obtained using the Friedewald equation. The levels of TG in the samples are from about 43 to about 769 mg/dl.

FIGS. 6 and 7 are graphs showing the correlation between the LDL-C determinations by beta-quantitation methods, and LDL-C determinations using the Friedewald calculation utilizing TC, TG and HDL-C measurements from the same CRMLN certified reference laboratory (i.e., Northwest Lipid Laboratories). Triglyceride levels in the serum samples range from about 40-800 mg/dl. The graph in FIG. 6 shows 46 of 61 data points, corresponding to samples with TG levels from 43 to 280 mg/dl. FIG. 7 shows 61 of 61 data points corresponding to samples with TG levels from 43 to 769 mg/dl. The addition (in FIG. 7) of the 15 data points, corresponding to the blood samples with the highest TG levels, significantly decreased the correlation between the beta-quantitation method and the Friedewald calculations using TC, TG and HDL-C values. The $R^2$ value for the correlation shown in FIG. 6 was about 0.968 (y=1.03x−12.84), while the $R^2$ value for the correlation shown in FIG. 7 was only about 0.893 (y=1.0054x−15.341).

The measurements obtained using the TG reagent pad and the TC reagent pad (for measuring TC as defined by LDL+

Figure 8:
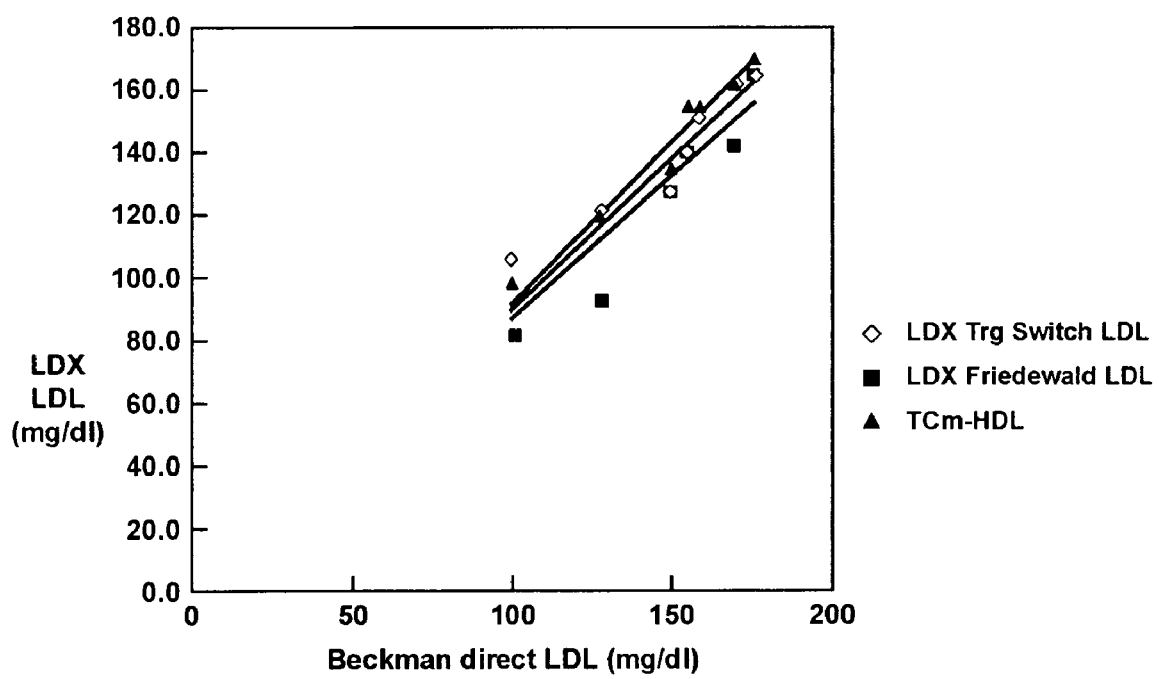
FIG. 8 is a graph showing a comparison of the LDL-C determinations obtained using a TCm embodiment of the cassette device in combination with (i) the beta-quantitation method (i.e., LDL-C=TC−HDL-C, represented by triangles), (ii) the Friedewald calculation of LDL-C (i.e., LDL-C=TC−HDL-C−TG/5, represented by squares), or (iii) the beta-quantitation method or the Friedewald calculation, depending on the amount of TG present in the sample (represented by diamonds).

HDL+VLDL+chylomicrons) were then used along with the HDL-C measurement to determine LDL-C using the Friedewald equation. As an external standard, LDL-C was measured using the Beckman direct LDL method. The Beckman assay is a homogeneous method that utilizes surfactants to selectively solubilize lipoprotein subclasses. Table 2 and the graph in FIG. 8 summarize the results from 8 blood samples, using results obtained from TCm embodiments (i.e., TCm-HDL-C, column 6, triangles), the Friedewald equation (i.e., LDL-C=TC-HDL-C-TG/5, column 4, squares); or a combination approach in which the LDL-C levels in the 6 samples with relatively low TG levels were calculated using the Friedewald equation, while the LDL-C levels in the 2 samples with relatively high TG levels (above 250 mg/dl, samples 9 and 10) were calculated using the beta-quantitation method (column 5, diamonds). These calculated LDL-C values were compared to those obtained using the Beckman direct LDL method (columns 2 and 3).

TABLE 2

LDL-C measurements

| Sample | Beckman TG | Beckman LDL | LDX Friedewald LDL | LDX TG Switch LDL | TCm-HDL |
|---|---|---|---|---|---|
| 1 | 122 | 176 | 164.9 | 164.9 | 170.0 |
| 2 | 104 | 155 | 140.2 | 140.2 | 154.9 |
| 3 | 116 | 150 | 127.5 | 127.5 | 134.6 |
| 4 | 100 | 159 | 151.1 | 151.1 | 154.3 |
| 5 | 171 | 101 | 81.9 | 81.9 | 82.0 |
| 6 | 39 | 100 | 105.8 | 105.8 | 98.7 |
| 9 | 273 | 170 | 142 | 162.1 | 162.1 |
| 10 | 271 | 128 | 92.7 | 121.2 | 121.2 |
| SD | | | | 5.79 | 7.82 |
| CV | | | | 4.2% | 6.0% |

As shown in FIG. 8, the use of the combined approach provided the best precision and accuracy versus the Beckman direct LDL method. The $R^2$ value for the combined method was about 0.911 compared to about 0.818 for the Friedewald method and about 0.960 for the TCm-HDL embodiment.

These results demonstrate that the TCm cassettes allow accurate measurement of LDL-C using the TCm-HDL embodiment (beta-quantification equation), the Friedewald equation, or a combination, thereof, depending on the particular measured TG levels. The beta-quantitation equation is of particular use where the TG levels are greater than about 250 mg/dl, although it is useful where the TG levels are from as low as about 100 mg/dl to as high as about 500 mg/dl. The Friedewald equation is of particular use where the TG levels are less than about 250 mg/dl, although it is useful where the TG levels are from as low as about 100 mg/dl to as high as about 400 mg/dl. In this manner, a single TCm cassette device can be used to rapidly and accurately determine the LDL-C levels in patients with a wide range of TG levels, all in a single automated assay.

The following Examples are provided to further illustrate but not limit the assays and methods. Additional embodiments will be apparent upon reading the disclosure.

EXAMPLES

Example 1

Preparation of Reagent Membranes with a Precipitant for HDL Measurement

To prepare a reagent membrane with soluble precipitant, an aqueous solution containing 1 mg/ml dextran sulfate (500,000 MW) and 12.5 mM $Mg(OAc)_2$ is dispensed onto a polysulfone asymmetric membrane 0.22 inches in width. The membrane thickness is 127+/−5 µm, with a bubble point of 85+/−5 psi. The reagent is dispensed at a coat weight of 60-80 mL/milli-square inch (also known as "msi," defined as one-thousandth of a square inch) and dried in an infrared oven set at 70-90 degrees Celsius for about 45-50 seconds in a continuous web coating/drying process. Lengths of, e.g., 100 feet are prepared in this manner and cut to fit the assay devices.

To prepare an HDL reaction membrane, a similar asymmetric polysulfone membrane is impregnated with the following aqueous formulation: cholesterol oxidase 36.5 units/ml, cholesterol esterase 215 units/ml, peroxidase 200 units/ml, 4-aminoantipyrine 1.88 µm/ml, and TOOS (3-[ethyl(3-methylphenyl)amino]-2-hydroxy propanesulfonic acid) 12.05 µm/ml. Dispense rate and drying time are as for the reagent membrane, above.

The two membranes are attached simultaneously to a support bar with a single thermal welding step.

Example 2

Preparation of Reagent Membranes with a Precipitant for TCm Measurement

To prepare a reagent membrane with soluble precipitant, an aqueous solution containing about 28 mg/mL dextran sulfate, MW 8000 (sodium salt) and 62 mM $MgSO_4$ is dispensed onto a polysulfone asymmetric membrane 0.22 inches in width. The membrane thickness is 127+/−5 µm, with a bubble point of 100+/−5 psi. The reagent is dispensed at a coat weight of 60-80 mL/msi and dried in an infrared oven set at 70-90 degrees Celsius for about 45-50 seconds in a continuous web coating/drying process. Lengths of, e.g., 100 feet are prepared in this manner and cut to fit the assay devices.

To prepare an TCm reaction membrane, an asymmetric polysulfone membrane having bubble point of 100+/−5 psi is impregnated with the following aqueous formulation: cholesterol oxidase 36.5 units/ml, cholesterol esterase 215 units/ml, peroxidase 200 units/ml, 4-aminoantipyrine 4 mg/ml, and TOOS (3-[ethyl(3-methylphenyl)amino]-2-hydroxy propanesulfonic acid) 57.5 mg/ml. Dispense rate and drying time are as for the reagent membrane, above.

The two membranes are attached simultaneously to a support bar with a single thermal welding step.

Example 3

Assay Procedure

The following assays were carried out in an LDX® analyzer, using reagent membranes specific for HDL and Tcm determinations. Those elements prepared essentially as described in Examples 1 and 2. Sample (35 µl of serum or whole blood) was applied to the sample well and allowed to distribute through the sample distribution matrix for 2 minutes. The reaction bar was then contacted with the matrix for 3 seconds, a time sufficient to transfer enough serum to fill the reagent pad and assay element (combined capacity about 1.5 µl), after which the bar was returned to its original position. Reflectance readings were taken from the upper surface of the HDL assay element every 3 seconds for 150 seconds, to monitor the progress of the HDL assay reaction. The minimum reflectance value attained was then converted to mg/dl of HDL cholesterol according to a previously established calibration curve.

Although the invention has been described with respect to particular embodiments and applications, it will be appreciated that various changes and modifications may be made without departing from the invention.

What is claimed is:

1. A cassette for determining an amount of low density lipoprotein associated cholesterol (LDL C) in a body fluid sample containing very low density lipoprotein (VLDL), chylomicrons, low density lipoprotein (LDL), high density lipoprotein (HDL), and triglycerides (TG) comprising:
   (a) a body having a sample well for receiving a sample fluid;
   (b) first and second detection zones mounted on said body for producing a detectable product related to the amount of HDL and an adjusted total cholesterol composed of HDL plus LDL without VLDL and chylomicrons, respectively, in said sample fluid,
   (c) fluid flow pathways for transferring sample fluid from the sample well to said detection zones,
   (d) at least a first reagent in one or more of said fluid flow pathways and optionally, in said sample well, for selectively removing VLDL and chylomicrons without removing LDL in sample fluid transferred from the sample well to the first and second detection zones, and at least a second reagent for selectively removing LDL in sample fluid transferred from the sample well to the first detection zone.

2. The cassette of claim 1, further comprising:
   a third detection zone mounted on said body for producing a detectable product related to the amount of TG in said sample fluid; and
   a fourth detection zone mounted on said body for producing a detectable product related to the amount of total cholesterol in said sample fluid.

3. The cassette of claim 1, which is in a dry-strip cassette format, wherein
   (i) said fluid pathways include at least one dry-strip spreading layer for transferring sample fluid from the sample well to the first and second detection zones, and
   (ii) said first and second detection zones include first and second reaction pads, respectively, carried on a reaction bar that is mounted on said body for movement toward and away from the body, to bring said pads into contact with said at least one spreading layer, to transfer sample fluid from the spreading layers to said pads.

4. The cassette of claim 2, wherein said third and fourth detection zones include third and fourth reaction pads, respectively, carried on a reaction bar that is mounted on said body for movement toward and away from the body, to bring said pads into contact with at least one spreading layer, to transfer sample fluid from the spreading layer to said pads.

5. The cassette of claim 3, wherein said first and second reaction pads contain reagents for producing a detectable product related to the amount of free and lipoprotein-associated cholesterol in said pads.

6. The cassette of claim 4, wherein said third reaction pad contains reagents for producing a detectable product related to the amount of triglycerides in said pad, and said fourth reaction pad includes reagents for producing a detectable product related to the amount of free and lipoprotein-associated cholesterol in said pad.

7. The cassette of claim 3, wherein the reagents for selectively removing VLDL and chylomicrons in sample fluid transferred from the sample well to the first and second reaction pads are contained in a dry-strip flap that provides fluid communication between the sample well and the at least one spreading layer, and the reagents for selectively removing LDL in sample fluid transferred from the sample well to the first reaction pad are contained in a filter pad carried on said reaction bar, immediately upstream of said first reaction pad.

8. The cassette of claim 3, wherein the reagents for selectively removing VLDL and chylomicrons in sample fluid transferred from the sample well to the second reaction pad are contained in a filter pad carried on said reaction bar, immediately upstream of said second reaction pad, and the reagents for selectively removing LDL in sample fluid transferred from the sample well to the first reaction pad are contained in a filter pad carried on said reaction bar, immediately upstream of said first reaction pad.

9. The cassette of claim 7, wherein said reaction bar is movable toward said body from a first position to a second position, to bring said flap into a position of fluid communication between the sample well and said at least one spreading layer, and from said second position to a third position, to bring said reaction pads into contact with said at least one spreading layer.

10. The cassette of claim 8, wherein said reaction bar is movable toward said body from a first position to a second position, to bring said reaction pads into contact with said at least one spreading layer.

11. The cassette of claim 1, which is in a microfluidics format, wherein said fluid pathways include a plurality of microchannels for transferring sample fluid from the sample well to the first and second detection zones, and said first and second reaction zones are formed in said body.

12. The cassette of claim 2, which is in a microfluidics format, wherein said fluid pathways include a plurality of microchannels for transferring sample fluid from the sample well to the third and fourth detection zones, and said third and fourth reaction zone is formed in said body.

13. The cassette of claim 11, wherein said first and second detection zones contain reagents for producing a detectable product related to the amount of free and lipoprotein-associated cholesterol.

14. The cassette of claim 12, wherein said third detection zone contains reagents for producing a detectable product related to the amount of triglycerides, and said fourth detection zone contains reagents for producing a detectable product related to the amount of free and lipoprotein-associated cholesterol.

15. The cassette of claim 11, wherein the reagents for selectively removing VLDL and chylomicrons in sample fluid transferred from the sample well to the first and second detection zones include affinity binding reagents in said first microchannel upstream of the first and second detection zones, and the reagents for selectively removing LDL in sample fluid transferred from the sample well to the second detection zone include affinity binding reagent contained in a region of the first microchannel between the first and second detection zones and downstream of the second detection zone.

16. Apparatus for determining the amount of low-density lipoprotein (LDL) in a body-fluid sample containing very low density lipoprotein (VLDL), chylomicrons, LDL and high-density lipoproteins (HDL), comprising:

(a) the cassette of claim 1, and
(b) a device reader having (i) a device holder for receiving said cassette, (ii) a sensor for measuring the amount of detectable product produced in said first and second zones of the device, and (iii) a processor operably connected to said sensor for determining sample amounts of HDL and adjusted total cholesterol and for calculating sample LDL level based on determined levels of HDL and adjusted total cholesterol.

17. The apparatus of claim 16, wherein said sensor is configured to measure the amount of detectable product produced in a third and fourth zone of the device, and the processor is operably connected to said sensor for determining sample amounts of triglycerides and total cholesterol, respectively.

18. The apparatus of claim 17, wherein said processor is operable to determine sample LDL level based on the difference between total adjusted cholesterol and HDL, when the detected level of triglycerides is above 250 mg/dl, and based on the difference between total cholesterol and HDL plus an adjusted triglyceride value, according to the Friedewald equation, when the detected level of triglycerides is below 250 mg/dl.

19. The apparatus of claim 16, wherein said processor is operable to determine sample LDL level from a lookup table whose LDL values are based on the difference between total adjusted cholesterol and HDL, when the detected level of triglycerides is above 250 mg/dl, and based on the difference between total cholesterol and HDL plus an adjusted triglyceride value; according to the Friedewald equation, when the detected level of triglycerides is below 250 mg/dl.

20. The apparatus of claim 16, wherein said processor is operable to determine sample LDL level from an algorithm which calculates LDL values based on the difference between total adjusted cholesterol and HDL, when the detected level of triglycerides is above 250 mg/dl, and based on the difference between total cholesterol and HDL plus an adjusted triglyceride value, according to the Friedewald equation, when the detected level of triglycerides is below 250 mg/dl.

21. The cassette of claim 13, wherein said at least one of said first detection zone or said second detection zone includes an asymmetric polysulfone membrane.

22. The cassette of claim 21, wherein reagents contained in said first detection zone includes at least one of: cholesterol oxidase, cholesterol esterase, peroxidase, 4-aminoantipyrine, and TOOS.

23. The cassette of claim 21, wherein reagents contained in said second detection zone includes at least one of: cholesterol oxidase, cholesterol esterase, peroxidase, 4-aminoantipyrine, and TOOS.

24. The cassette of claim 22, wherein said membrane said first detection zone is in contact with a reagent membrane which includes a solution containing at least one of the following: dextran sulfate, $Mg(OAc)_2$.

25. The cassette of claim 23, wherein said membrane said second detection zone is in contact with a reagent membrane which includes a solution containing at least one of the following:

dextran sulfate, $MgSO_4$.

* * * * *